(12) United States Patent
Mathieu et al.

(10) Patent No.: US 11,842,310 B2
(45) Date of Patent: Dec. 12, 2023

(54) EXPOSURE RISK ASSESSMENT AND COUNTERMEASURE SYSTEMS

(71) Applicant: GM GLOBAL TECHNOLOGY OPERATIONS LLC, Detroit, MI (US)

(72) Inventors: Roy J. Mathieu, Rochester Hills, MI (US); Omer Tsimhoni, Bloomfield Hills, MI (US); Aravind Gangumalla, Novi, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 127 days.

(21) Appl. No.: 17/118,933

(22) Filed: Dec. 11, 2020

(65) Prior Publication Data

US 2022/0188716 A1 Jun. 16, 2022

(51) Int. Cl.
*G06Q 10/0635* (2023.01)
*C11D 11/00* (2006.01)
(Continued)

(52) U.S. Cl.
CPC ...... *G06Q 10/0635* (2013.01); *C11D 11/0041* (2013.01); *G06Q 50/30* (2013.01); *G16H 50/80* (2018.01)

(58) Field of Classification Search
CPC .... G06Q 40/08; G06Q 10/0635; G06Q 50/01; G06Q 10/06; G16H 50/30;
(Continued)

(56) References Cited

U.S. PATENT DOCUMENTS

| 11,104,347 B1* | 8/2021 | Morizumi | .............. G06Q 50/22 |
| 2014/0244344 A1* | 8/2014 | Bilet | .................... G06Q 30/018 |
| | | | 705/7.28 |

(Continued)

FOREIGN PATENT DOCUMENTS

DE 102019211667 A1 * 2/2021

OTHER PUBLICATIONS

S. H. Lee, et al. "Influenza surveillance and forecast with smartphone sensors," 16th IEEE International Symposium (ISORC 2013), 2013, pp. 1-8, doi: 10.1109/ISORC.2013.6913227 https://ieeexplore.ieee.org/document/6913227?source=IQplus (Year: 2013).*

(Continued)

*Primary Examiner* — Jerry O'Connor
*Assistant Examiner* — Michael R Koester

(57) ABSTRACT

A risk assessment system is provided and includes a transceiver, an output device, and activity, localization, tracking, and risk assessment modules. The activity module: receives signals from sensors or electrical devices of a supporting structure; and tracks activities in or within a set distance of the supporting structure to generate an activity history log. The localization module relates the activities to aspects of the supporting structure and generates corresponding localization data. The transceiver receives a notification key identifying a network device used by a user exposed to a contaminant. The tracking module, in response to the notification key, tracks contamination states of the aspects of the supporting structure contacted directly or indirectly by the user. The risk assessment module determines and reports an exposure risk level of an occupant of the supporting structure based on the contamination states, the localization data and the activity history log.

20 Claims, 9 Drawing Sheets

(51) Int. Cl.
*G06Q 50/30* (2012.01)
*G16H 50/80* (2018.01)

(58) Field of Classification Search
CPC .. G06F 19/3431; G06F 21/552; G06F 21/577; G06F 21/6245; G06F 21/316; H04L 63/1433
See application file for complete search history.

(56) References Cited

U.S. PATENT DOCUMENTS

2021/0150874 A1* 5/2021 Turano ................ H04L 12/2809
2022/0028556 A1* 1/2022 Tiwari .................. G16H 50/30
2022/0129687 A1* 4/2022 Munir ................... G01S 13/867

OTHER PUBLICATIONS

Sahraoui, Yesin, et al. "Remote sensing to control respiratory viral diseases outbreaks using Internet of Vehicles." Transactions on Emerging Telecommunications Technologies (2020): e4118. https://arxiv.org/abs/2103.12512 (Year: 2020).*
U.S. Appl. No. 17/118,893, filed Dec. 11, 2020, Velleu et al.

* cited by examiner

EXPOSURE RISK ASSESSMENT AND COUNTERMEASURE SYSTEMS

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to surface and interior space contamination detection systems.

Contaminants may be spread by common touchpoints of a vehicle, a building, and/or other supporting structure. For example, an occupant of a vehicle that is sick and/or has, for example, a virus may contact various points on and/or in a vehicle, such as door handles, armrests, seats, switches, steering wheel, etc. The occupant may also, through the air, contaminate surfaces by breathing, coughing, and/or sneezing within the vehicle. This can result in the spread of germs in an interior of and onto surfaces within the vehicle. A second occupant may contact the same surfaces and/or breathe in contaminated air within the vehicle and as a result become infected.

As another example, a first individual that is sick and/or has been exposed to a virus may stay as a guest in a hotel room and contact various surfaces of the hotel room. A second individual may reserve and stay in the same hotel room subsequent to the first individual. During the second individual's stay in the hotel room, the second individual may contact contaminated surfaces that were not adequately cleaned and as a result contract the virus. This may similarly occur when a hotel staff member exposed to a virus enters and/or cleans a hotel room. The hotel staff member may contaminate surfaces by physical contact and/or by spreading of contaminated droplets while breathing, coughing and/or sneezing in the hotel room. A guest subsequently staying in the hotel room may then contract the virus.

SUMMARY

A risk assessment system is provided and includes a memory, an activity module, a localization module, a transceiver, a first tracking module, a risk assessment module and an output device. The memory is configured to store an activity history log associated with a supporting structure. The activity module is configured to: receive signals from at least one of sensors or electrical devices of the supporting structure; and track activities at least one of in or within a set distance of the supporting structure to generate the activity history log. The localization module is configured to relate the activities to aspects of the supporting structure and generate corresponding localization data, where the aspects include at least one of surfaces, areas, spaces or volumes of the supporting structure. The transceiver is configured to receive a notification key identifying a network device used by a user exposed to a contaminant. The first tracking module is configured to, in response to the notification key, track contamination states of the aspects of the supporting structure contacted directly or indirectly by the user. The risk assessment module is configured to determine an exposure risk level of an occupant of the supporting structure based on the contamination states of the aspects, the localization data and the activity history log. The output device is configured to indicate the exposure risk level to the occupant.

In other features, the risk assessment system further includes sensors for detecting the activities. The activity module is configured to update the activity history log based on outputs of the sensors.

In other features, the activity module is configured to monitor changes in states of the electrical devices and, in response to the changes in the states of the electrical devices, update the activity history log.

In other features, the activity module is configured to: track activity of the user in the supporting structure; and subsequent to tracking the activity of the user, receive the notification key. The risk assessment module is configured to, subsequent to reception of the notification key, determine the exposure risk level of the occupant.

In other features, the risk assessment system further includes a second tracking module configured to track events including cleaning at least some of the aspects of the supporting structure. The risk assessment module is configured to determine the exposure risk level of the occupant based on information defining aspects of the events including cleaning the aspects of the supporting structure.

In other features, the second tracking module is configured to determine sanitization levels of at least some of the aspects of the supporting structure based on the tracked events including cleaning. The risk assessment module is configured to, based on the sanitization levels, determine the exposure risk level.

In other features, the risk assessment module is configured to determine the exposure risk level based on exposure times of the supporting structure to the user, duration of time since the support structure was exposed to the user; and times the occupant was exposed to the supporting structure.

In other features, the risk assessment system further includes sensors. The activity module is configured to identify user interaction with at least some of the aspects based on historical human-vehicle interaction activities, and update the activity history log.

In other features, the risk assessment module is configured to, based on the exposure risk level, convey a message via the output device to the occupant to clean at least some of the aspects.

In other features, the risk assessment module is configured to indicate via the output device which of the aspects to clean, which of the aspects that do not need to be cleaned, and which of the aspects for which cleaning indications are not available.

In other features, the risk assessment module is configured to, based on the exposure risk level, initiate an automated cleaning process to disinfect one or more of the aspects.

In other features, the risk assessment module is configured to risk-prioritize vehicle interactions with the user and determine the exposure risk level based on results of the risk-prioritization of the vehicle interactions with the user.

In other features, the risk assessment module is configured to determine the exposure risk level of the occupant based on an exposure function for a carrier, a decay function since last exposure, a decay cleaning function, and an exposure function for the occupant.

In other features, the risk assessment module is configured to determine the exposure risk level of the occupant based on at least one of a time domain-based exposure pattern, a frequency domain-based exposure pattern, or a spatial domain-based exposure pattern.

In other features, a risk assessment server is provided and includes a memory, a transceiver and a control module. The memory is configured to store an activity history log of a supporting structure, where the supporting structure is remotely located away from the risk assessment server. The transceiver is configured to receive the activity history log from the supporting structure and a notification key from an arbitration server, where the notification key identifies a first network device of a user exposed to a contaminant. The control module is configured to: in response to the notification key, track contamination states of aspects of the supporting structure contacted directly or indirectly by the user, where the aspects include at least one of surfaces, areas, spaces or volumes of the supporting structure; determine an exposure risk level for an occupant of the supporting structure based on the contamination states of aspects, localization data and the activity history log; and send an alert message indicating the exposure risk level to at least one of the support structure or a second network device of the occupant.

In other features, the activity history log includes at least one cleaning event and corresponding characteristics; and the control module is configured to determine the exposure risk level based on the corresponding characteristics.

In other features, the corresponding characteristics identify aspects cleaned, length of time each of the identified aspects were cleaned, and identify aspects not cleaned.

In other features, the control module is configured to determine sanitization levels of the aspects based on the corresponding characteristics.

In other features, the control module is configured to risk-prioritize vehicle interactions with the user and determine the exposure risk level based on results of the risk-prioritization of the vehicle interactions with the user.

In other features, the control module is configured to: determine the exposure risk level of the occupant based on an exposure function for a carrier, a decay function since last exposure, a decay cleaning function, and an exposure function for the occupant; and determine the exposure risk level of the occupant based on at least one of a time domain-based exposure pattern, a frequency domain-based exposure pattern, or a spatial domain-based exposure pattern.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1:
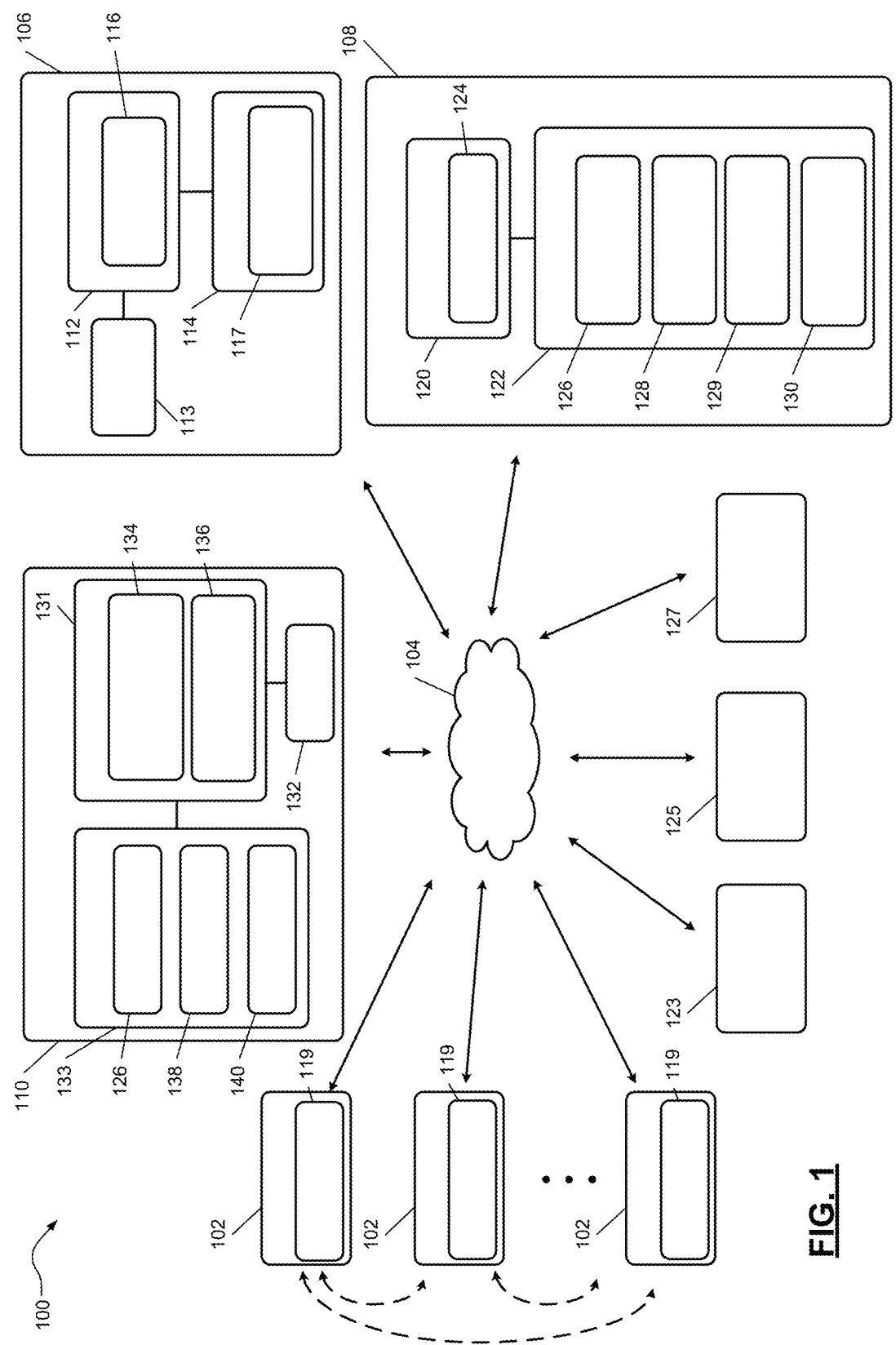
FIG. 1 is a functional block diagram of an example of a contamination and risk assessment system in accordance with the present disclosure.

Locating contaminated areas can be difficult. It can be unclear what surfaces have been contacted and/or require sanitization and/or avoidance so as not to catch a virus and possibly become sick. For example, it can be difficult to determine which surfaces within a vehicle are contaminated. Also, cleaning interiors of a vehicle, a room, a building, etc., can be inefficient without knowing (i) which specific areas are contaminated and/or need cleaning, and (ii) which areas are not contaminated and do not need cleaning.

The examples set forth herein include contamination detection and indication systems. The systems indicate surface areas that are contaminated and/or surfaces areas that have been sanitized. This allows for easy detection and avoidance of these areas and/or identification of contaminated areas for cleaning purposes. In a vehicle environment, the systems detect and provide views of vehicle interiors with indications of areas touched by previous passengers in order to identify likely areas of contamination. Sensors and other component state detection operations are performed concurrently and non-invasively to track where interior vehicle surfaces have been contacted. In some embodiments, the systems display a contamination mapping and/or sanitization mapping highlighting contaminated areas and/or sanitized areas. This information may be provided in the form of an augmented reality (AR), where for example, a display of a portable network device shows an interior area including highlighted portions indicating areas that are contaminated and/or sanitized. This is further described below. The examples include performing countermeasures to decontaminate the surfaces and prevent further contamination and/or spread of germs to other users, occupants, customers, etc.

Some of the embodiments include exposure risk assessment (herein also referred to as simply "risk assessment"). The term risk assessment refers to a probability of an occupant being exposed to, for example, a virus such as a cold, a flu, a coronavirus, etc. A risk assessment may be determined based on an amount of exposure, length of exposure, whether contacted surfaces are anti-microbial and/or anti-viral surfaces, a decay rate of the surfaces, whether direct contact or indirect contact occurred, etc. An anti-microbial surface includes an anti-microbial agent that inhibits the ability of microorganisms to grow. Similarly, an anti-viral surface includes an anti-viral agent that inhibits the ability of a virus to grow, live and/or spread. As an example, an anti-microbial surface and an anti-viral surface may include copper and/or a copper alloy, which are both antimicrobial and anti-viral materials. The decay rate refers to the rate at which microorganisms and/or viral organisms die off when exposed to the anti-microbial and anti-viral surface materials. Direct contact may refer to when a person identified as having been exposed to a contaminate physically contacts and/or touches a surface, an inanimate object and/or an animate object. Indirect contact may refer to when the person breathes, coughs and/or sneezes on or near a surface. Indirect contact may also refer to when a second individual contacts a surface contacted by the person identified as having been exposed and/or entering a space where the exposed person was previously. Indirect contact by the second individual can occur through physical contacts with surfaces and/or through the air. Although below examples are primarily described with respect to contamination and sanitization levels of surfaces, other aspects such as areas, spaces and/or volumes of supporting structures may also be monitored and tracked. Exposure levels may be determined and countermeasures may be performed based on contamination and sanitization levels of any of these aspects.

Although some of the below described embodiments are directed to vehicular applications, the described embodiments are also applicable to other non-vehicular applications. For example, the embodiments are applicable to hotels, elevators, doorways, restrooms, banks, automatic teller machines (ATMs), stores, food markets, private residences, businesses, restaurants, public transportation, vending machines, operating rooms and equipment, etc. The embodiments are applicable to automotive vehicles, trains, subways, airplanes, watercraft and/or other vehicles.

FIG. 1 shows a contamination and risk assessment system 100 that includes network devices 102, a distributed network 104, a public health arbitration server 106, a risk assessment server 108 and a central monitoring station 110. The network devices 102 may include network devices within vehicles, buildings, rooms, and/or other supporting structures. The network devices 102 may include, for example, telematics modules, infotainment modules, control modules, etc. of various devices and/or vehicles. The network devices 102 may further include portable network devices, such as cellular phones, mobile access devices, tablets, laptop computers, wearable devices, smart glasses, virtual reality devices (e.g., virtual reality headsets), etc. The network devices may be directly in communication with each other or indirectly via the distributed network 104. The distributed network 104 may include local area networks (LANs), wireless local area networks (WLANs), cellular networks, etc. The distributed network 104 may include routers, modems, satellites, base stations, gateways, etc.

The public health arbitration server (PHAS) 106 may include a control module 112, a transceiver 113, and memory 114. The control module 112 may include a contact tracing module 116, which may track devices that have been or have likely been contaminated and/or exposed to a contaminate and/or devices that have not been contaminated and/or exposed. This information may be stored in a contact tracing database 117. Similarly, the contact tracing module 116 may also track animate objects that have been contaminated and/or exposed and/or animate objects that have not been contaminated and/or exposed. The collected information may be based on hospital reports, doctor office reports, health clinic reports, testing center reports, reports from individuals, etc. As an example, one of the network devices 102 may indicate to the PHAS 106 that a user of the network device was exposed to a virus. The PHAS 106 may then record this information for the network device (referred to as the exposed network device) and determine if there were any other network devices in close proximity of the exposed network device. If yes, the PHAS 106 may also store this information and contact the other network devices that were in close proximity and as a result may also have been exposed. The above-stated information may be stored as part of a contact tracing database 117 stored in the memory 114. In one embodiment, the network devices 102 include contact tracing modules 119 that receive the information from the PHAS 106 including any of the stated information stored in the contact tracing database 117. This is done such that notification (or diagnosis) keys are shared by the PHAS 106 to the network devices 102 and the network devices 102 may then be responsible for decision making with regards to countermeasures being performed. The notification keys may indicate that one or more network devices may have been exposed including the network devices receiving the notification keys.

Although shown separately, the risk assessment server 108 and the central monitoring station 110 may be implemented as a single server. The risk assessment server 108 may perform risk assessment based on collected data and information pertaining to contamination and sanitization of network devices and surfaces of exteriors and interiors of supporting structures. A supporting structure may refer to a vehicle, a building, a room, an elevator, a machine, and/or other structures for supporting sensors, displays, audio equipment, and/or other equipment for performing at least some contamination, sanitization, and/or risk assessment related operations as described herein. This include detecting, monitoring, tracking, analyzing, assessing, and reporting operations disclosed herein.

The risk assessment server 108 includes a control module 120, a transceiver 121 and memory 122. The control module 120 may include a learning module 124. The memory 122 may store an activity history log 126, contamination mapping data 128, sanitization mapping data 129, and risk assessment data 130. The risk assessment server 108 and the central monitoring station 110 may store activity data received from the network devices 102 in the form of the activity history log 126. The activity history log 126 may include a list of activities that have occurred over time, where each activity includes an activity identifier, a timestamp (including a date and time), and a duration over which the activity occurred. As an example, various activities may occur in and/or in association with a vehicle. The activities may include: opening and closing doors; opening and closing windows; activating and deactivating lights, entertainment equipment, stereos, an air-conditioning system; adjusting seat and mirror positions; adjusting steering angles; adjusting temperatures of seats; adjusting positions of seats; etc. All of these activities include a vehicle occupant contacting various surfaces, such as door handles, control knobs, steering wheel, buttons, switches, mirrors, armrests, seats, dashboards, consoles, dashboards, cup holders, etc. This contacting can transfer germs as described above to the surfaces and/or from the surfaces to the occupant. The activity history log 126 may be a rolling log that includes data for a last predetermined period of time (e.g., 14 days).

Figure 5:
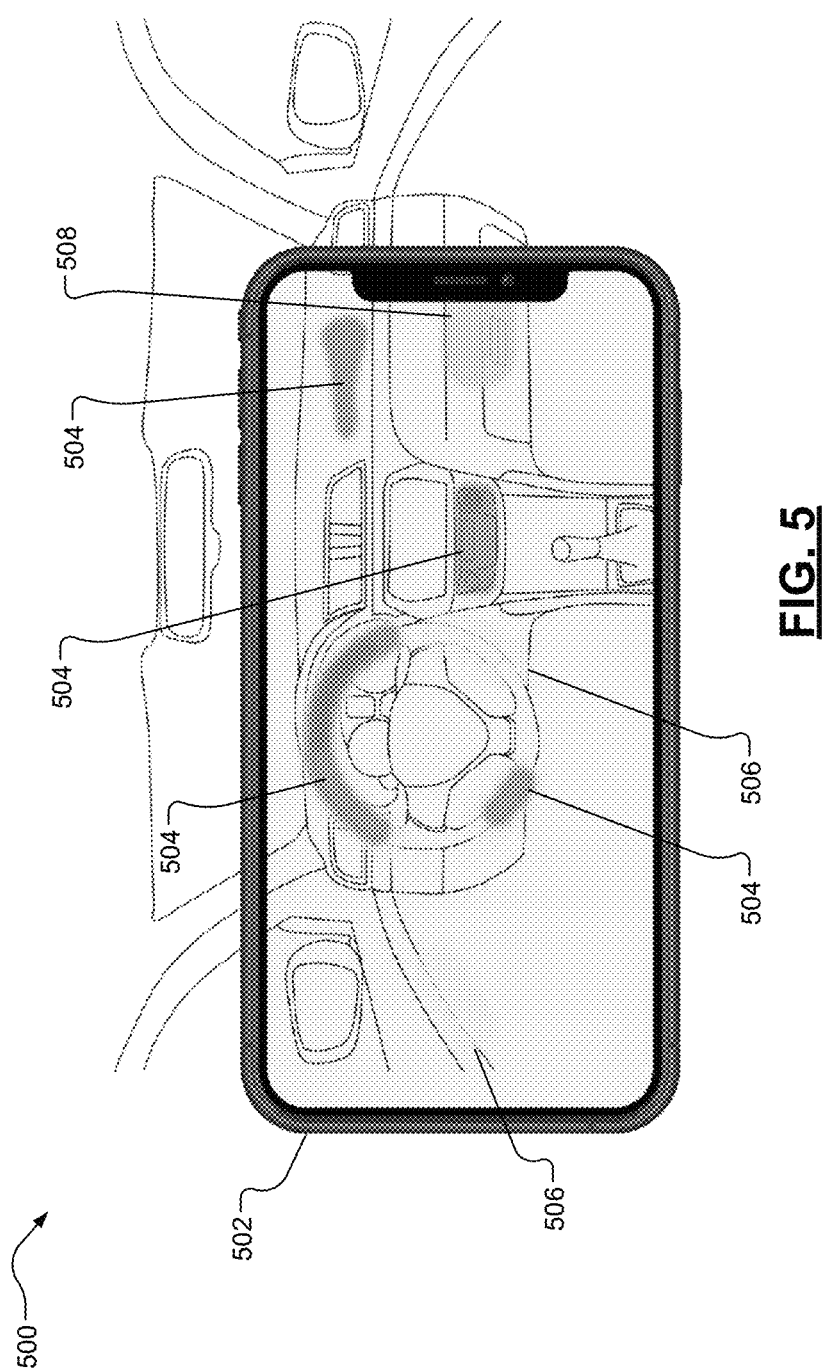
FIG. 5 is forward facing perspective view of an example of an interior of a vehicle illustrating an augmented reality view via a portable network device in accordance with the present disclosure.

The contamination mapping data 128 may include data that indicates levels of contamination for various surfaces, for example, within a supporting structure and related to locations on a map of the supporting structure. The contamination mapping data 128 may be displayed in an overlapping manner, for example, over an image (or view) of an area. An example illustration is shown in FIG. 5. A similar mapping including levels of sanitization may be provided for the sanitization mapping data 129. The risk assessment data 130 may indicate levels of risk for network devices and/or users, occupants, and/or customers. As an example, the risk assessment data 130 may indicate the probability that a vehicle occupant and/or a cellular phone of the vehicle occupant has been exposed to a virus. Multiple risk assessment examples are described below. This information may be reported to the occupant via displays and/or an audio system within the vehicle and/or via the cellular phone.

The central monitoring station 110 may be associated with a service provider, such as a car rental or leasing company, a rideshare service company, a car service station, and/or other service provider. The central monitoring station 110 may include a control module 131, a transceiver 132 and memory 133. The control module 131 may include a contamination and sanitization tracking module 134 and a cleaning indication module 136.

The contamination and sanitization tracking module 134 may track and/or evaluate data in the activity history log 126, contamination data 138, and/or sanitization data. The contamination and sanitization tracking module 134 may perform a more detailed data analysis and/or localization mapping than that performed at the network devices 102 and share the results with the network devices 102. Localization mapping is further described below. The localization mapping may (i) relate contact points to contamination levels and/or sanitization levels, and/or (ii) relate location and orientation of network devices to supporting structures and corresponding surfaces.

The cleaning indication module 136 may provide suggested cleaning instructions as further described below based on the activity history log 126, contamination data 138, sanitization data and/or results of the analysis performed by the contamination and sanitization tracking module 134. The cleaning indication module 136 may perform machine learning and/or artificial intelligence based operations in order to generate the cleaning instructions. The machine learning operations may be based on historical and currently collected data. The memory 133 may store the activity history log 126, contamination data 138 and sanitization data 140. The contamination data 138 and the sanitization data 140 may include the above-stated contamination data 128 and the sanitization data 129.

As an example, the control module 131 may report contamination levels and/or sanitization levels of surfaces of numerous vehicles monitored by a fleet manager. The control module 131 and/or the fleet manager may then send signals to vehicle drivers to clean surfaces of the vehicles. The control module 131 and/or the fleet manager may indicate which surfaces need to be cleaned and which surfaces may not need to be cleaned based on collected data.

The contamination and risk assessment system 100 may further include sensors 123, indicator input devices 125, and output devices 127. The sensors 123, indicator input devices 125, and/or output devices 127 may be located at and/or in close proximity to the network devices 102 and/or a supporting structure. The sensors 123 and/or output devices 127 may be implemented as part of the network devices 102 and/or supporting structures. The sensors 123 and/or output devices 127 may be implemented separate from the network devices 102 and/or supporting structures. The sensors 123 may include position sensors, contact sensors, pressure sensors, weight sensors, location sensors, linear sensors, rotary sensors, potentiometers, piezoresistive sensors, load sensors, piezoelectric sensors, cameras, infrared sensors, Lidar sensors, radar sensors, air flow sensors, microphones, surface embedded sensors, force sensors, etc. The sensors 123 may include window position sensors, door position sensors, mirror position sensors, steering sensors and/or other position sensors. The sensors 123 may be located on or in network devices, supporting structure, and and/or nearby infrastructure (such as traffic poles, traffic signals, bridges, walls, etc.). Some of the sensors 123 are further described below. The sensors 123 may be used to detect the presence of occupants and register them. The sensors 123 may be used to identify user interactions with vehicle surfaces based on historical human-vehicle interaction activities (entry, egress, switch operation, etc.).

The indicator input devices 125 may include switches, knobs, slides, dials, motors, actuators, transceivers, touch screens, touch pads, buttons, etc. The output devices 127 may include displays, screens, lights, mirrors, wiper motors, gear shifters, electrical steering devices, audio devices (e.g., speakers), smart surfaces, and/or other electrical devices. Smart surfaces in the context of this disclosure refer to surfaces that are able to physically change in state, such as in color and/or shade. The different colors and/or shades may be associated with different contamination and/or sanitization levels. Smart surfaces may be able to display information to indicate contamination and/or sanitization levels. In another embodiment, the output devices 127 include directional lights and/or light emitting diodes (LEDs) that are controlled and able to light up different areas using different colors and/or illumination patterns. The lights may be strobed at different frequencies. As an example, a dome light housing in a vehicle may have any number of LEDs that are controlled to indicate levels of contamination and/or sanitization on surfaces within the vehicle. In another embodiment, directional audio is used to more precisely locate areas and/or zones of concern (i.e. contaminated areas to be sanitized). This may be detected by the sensors 123 and then the areas and/or zones may be highlighted and/or identified by the output devices 127.

As an example, the sensors 123, the indicator input devices 125 and output devices 127 may be located throughout a vehicle. The sensors and indicator input devices 125 may be used to monitor and track contact activity associated with the vehicle. As an example, cameras may be used to monitor the interior of a vehicle and detect surfaces that have been touched and/or contacted, number of times contacted, and the lengths of each contact. This information may be timestamped for contamination and sanitization based determinations. This type of contact activity is recorded and may be reported by one or more of the network devices 102 to the risk assessment server 108 and/or the central monitoring station 110.

The network devices 102 may indicate the contamination and/or sanitization levels of the surfaces via devices of the vehicle and/or via portable network devices located in the vehicle. The risk assessment server 108 and/or the central monitoring station 110 may use the received activity information to assess risk of exposure and/or to determine contamination and/or sanitization levels of surfaces. The contamination and/or sanitization levels and/or alert information may be generated by one of the control modules 120, 131 and transmitted back to the network devices 102. The alert information may indicate the stated levels, areas to sanitize, areas that have been sanitized, areas that have unknown (or undeterminable) contamination and sanitization levels, areas that have not been contacted for extended periods of time, etc.

Figure 2:
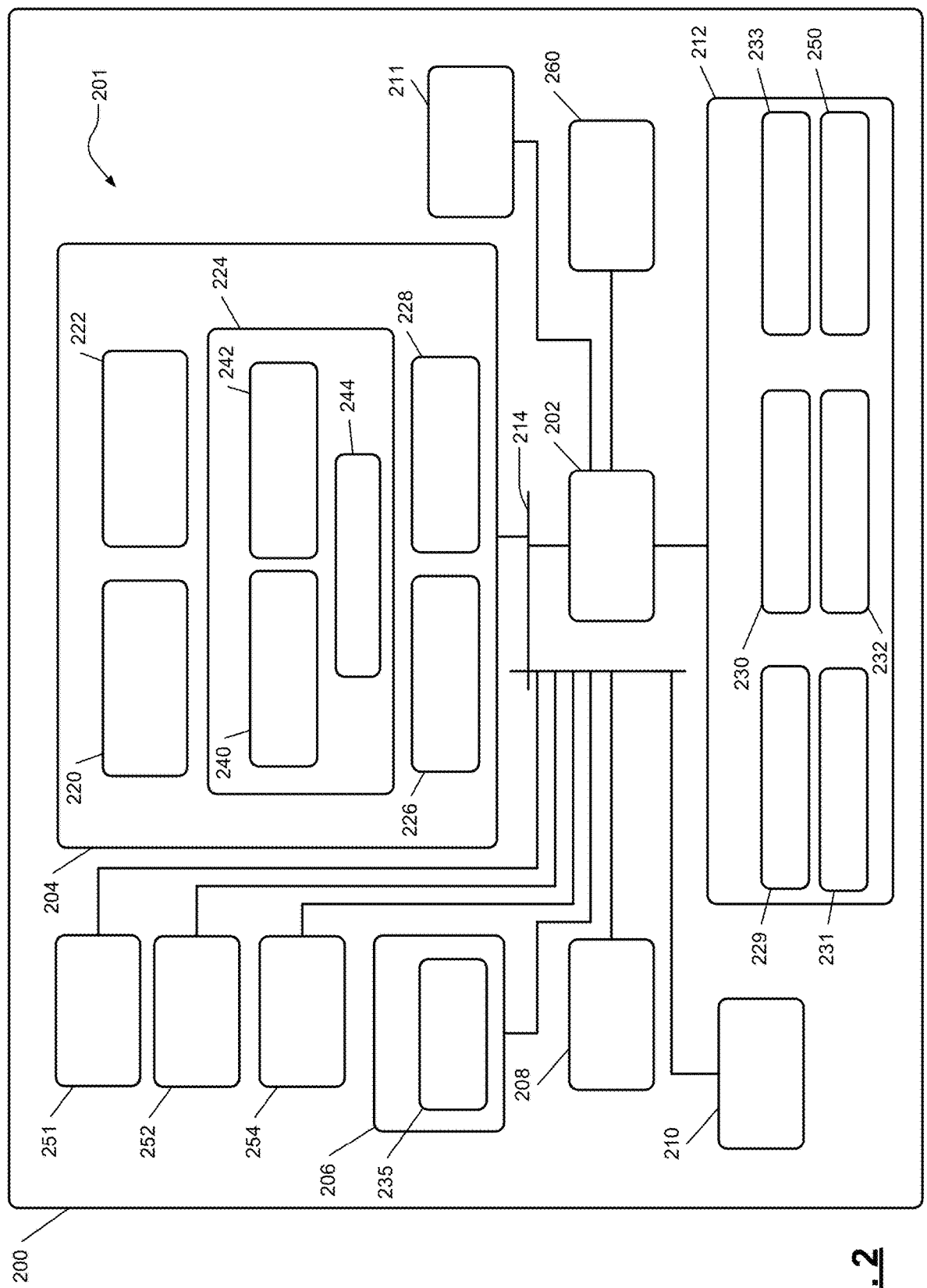
FIG. 2 is a functional block diagram of an example of a supporting structure including modules for contamination, sanitization and activity tracking and risk assessment in accordance with the present disclosure.

FIG. 2 shows a supporting structure 200 including a contamination and risk assessment system 201 (may also be referred to as a contamination detection and notification system) that includes a control module 202, an infotainment module 204, a telematics module 206, indicator input devices 208, sensors 210, output devices 211 and a memory 212. The supporting structure 200 may be a vehicle, a building, a room, a machine, or other supporting structure. The control module 202 may be a central (or main) control module of the supporting structure. For example, if the supporting structure 200 is a vehicle, the control module 202 may be a body control module or other vehicle control module. The infotainment module 204, the telematics module 206, the indicator input devices 208 and the sensors 210 may be connected to the control module 202 via a controller area network (CAN) bus 214 or similar vehicle communication technologies.

The infotainment module 204 may include a contamination tracking and indication module 220, a sanitization tracking and indication module 222, an activity tracking module 224, a localization module 226, and a risk assessment module 228. The modules 220, 222, 224 may be referred to as tracking modules. The module 224 may be referred to as an activity module. The activity tracking module 224 may include a motion tracking module 240, a physical contact and/or surface module 242 and an air monitoring module 244. Any of these modules may be included in the control module 202. Also, any combination of these modules may be integrated as part of a single module.

The contamination tracking and indication module 220 may monitor, track and/or determine contamination levels of surfaces, such as surfaces of a vehicle, a room, a machine, etc. The contamination tracking and indication module 220 may collect activity data associated with use and/or corresponding localization data to estimate contamination levels based on monitored activities. This tracking may be based on a trigger event, such as a notification that a user, occupant and/or customer was potentially exposed to a virus and/or was identified as having the virus. Exposure information 233 may be detected and/or received from a network device and/or a server via one or more transceivers 235 of the telematics module 206 and stored. The exposure information 233 may indicate the network devices that have likely been exposed and the times, number of contacts at each location and/or point, durations of contacts, and dates that the exposure occurred. The contamination tracking and indication module 220 may store the contamination levels as contamination data 229 in the memory 212.

The sanitization tracking and indication module 222 may monitor, track and/or determine sanitization levels of surfaces, such as surfaces of a vehicle, a room, a machine, etc. The sanitization tracking and indication module 222 may collect activity data associated with use and/or corresponding localization data to estimate sanitization levels based on monitored cleaning. This tracking may be based on a trigger event, such as the above-stated trigger event. The sanitization tracking and indication module 222 may store the sanitization levels as sanitization data 231 in the memory 212.

The activity tracking module 224 may collect data from the sensors 210 and indicator input devices 208, which may be similar to the sensors 123 and the indicator input devices 125 of FIG. 1. This activity tracking may be based on the above-stated trigger event and/or may be continuously tracked. The activity tracking module 224 records over a predetermined period of time activity tracking data 230, which is stored in the memory 212, such as which doors were opened, what windows were actuated, what buttons were pushed, etc. This may include identifying surfaces contacted and determining the length of contacts, number of times contacted, and recording timestamp information including times and dates of contacts. It can be inferred that certain handles, knobs, buttons, and/or other controls have been touched when certain vehicle events occur (e.g., a door opens or closes, a window is actuated, a state of a radio changes, etc.), except for when voice commands are provided. The activity tracking module 224 may refrain from recording activity that is associated with voice commands. When voice activated, a surface may not be touched and thus recording of this type of activity may not be needed. If a button is pushed to activate voice operations, then information associated with pushing the button may be recorded. The facing direction and/or direction of speech may be detected and tracked. Surfaces forward of the speaker may be identified as being in potential contact of the breath of the speaker and/or droplets due to coughing and/or sneezing of the speaker. These determinations may be made based on recorded and analyzed video and/or audio detecting the location and facing direction of the speaker.

The motion tracking module 240 may execute algorithms to track movement of users, occupants and/or customers within a vehicle, a building or a room. This may be done using cameras and/or other motion tracking equipment to track movement. For example, the motion tracking module 240 may track movement of cleaning staff of a hotel and/or hotel guests based on which doors have been opened, which access cards have been swiped through which card readers, etc. Activity associated with electronic devices such as coffee makers, televisions, refrigerators, hair dryers, irons, computers, thermostats, etc. may be monitored and tracked. This may be implemented to determine in which rooms cleaning staff and/or hotel guests have been. The motion tracking module may also be used to track movement within a vehicle to determine where contacts with surfaces have occurred and/or orientation of occupants within the vehicle. As an example, an occupant of a vehicle may open a door, sit in a certain seat, close the door, use a seat belt, perform certain activities, and then reopen and close the door while leaving the vehicle. All of which may be tracked and recorded. This information may be included in the activity tracking data 230. The physical contact and/or surface module 242 may track which surfaces have be touched and/or contacted based on signals from contact sensors and/or other sensors. This information may also be included in the activity tracking data 230.

The air monitoring module 244 may monitor air quality levels within an enclosed area, such as within a vehicle, a room, etc. This may be based on signals received from sensors, such as air flow sensors, fans, air-conditioning systems, air filtration systems, etc. The air quality level information may also be included in the activity tracking data 230. The air monitoring module 244 may monitor a microphone and/or other sensors to track coughing, sneezing, and/or other sounds implying the spread of germs through the air. This information may be related to images to determine what surfaces have been potentially affected by the transfer of these germs.

The localization module 226 may associate contacts with locations. For example, cameras may be used to capture images and based on the images the localization module is able to identify surfaces contacted and where on the surfaces contacts were made. The localization module 226 may store localization data 232 indicative of the stated locations in the memory 212 and be accessible to the other stated modules.

The risk assessment module 228 may determine risk levels of becoming contaminated and/or contracting a virus if an individual, for example, enters a vehicle, enters a room, is within a certain location, does a certain activity, contacts a certain surface, etc. Risk assessment is further described below. Risk assessment information 250 may be stored in the memory 212 and indicated to users, occupants, customers via the output devices 211 (e.g., the output devices 127 of FIG. 1). As an example, a vehicle may be taken to a service station and the technician working on the vehicle may have been identified as being exposed to a contaminate. The risk assessment module 228 may determine the exposure risk levels associated with the vehicle owner entering and operating the vehicle and inform the vehicle owner. As another example, a service provider attendant may have been exposed to a contaminate and load a vehicle with groceries. The risk assessment module 228 may determine the exposure risk levels associated with an individual accessing the vehicle and/or removing the groceries.

The above-stated data and information stored in the memory 212 may be generated, received, and/or shared by the modules 204, 220, 222, 224, 226, 228, 240, 242, 244. The supporting structure 200 may include a projector 260, which may be one of the output devices 211. The projector 260 may project an image over surfaces of an area to indicate contamination and/or sanitization levels of the surfaces. In one embodiment, multiple projectors are used to project images over surfaces to indicate contamination and/or sanitization levels. In another embodiment, a simple projector having one or more LEDs are used to project light and highlight one or more areas. As yet another example, a green or red light may be projected onto an internal or external door handle or the handle may include a green or red light to indicate whether the handle has or has not been used.

The memory 212 may store information associated with compound touches between clean and contact events. Although the contamination and contaminate examples referred to herein are primarily described as viral related, the examples are applicable to other contaminates. Time tracking is performed to provide information indicating when viral, chemical, and/or radioactive contaminates have likely decayed.

In one embodiment, the supporting structure 200 includes a cleaning system 251, which may initiate and/or perform cleaning operations based on instructions from the infotainment module 204. This may include, for example, activating an ultraviolet C-bond (UVC) light and/or injecting and/or spraying disinfectant in an area of the supporting structure 200. The cleaning system 251 may include, for example, a UVC light, a reservoir with disinfectant and/or a pump for spraying the disinfectant. The light and the pump may be controlled by a module of the cleaning system 251, the control module 202 and/or other control module. In another embodiment, the supporting structure 200 is an autonomous vehicle and the cleaning system 251 initiates an action to move the vehicle through a cleaning station, such as a car wash. In another embodiment, the cleaning system 251 opens windows 252 and/or runs fans 254 within the interior of the vehicle to air out the interior of the vehicle.

Figure 3:
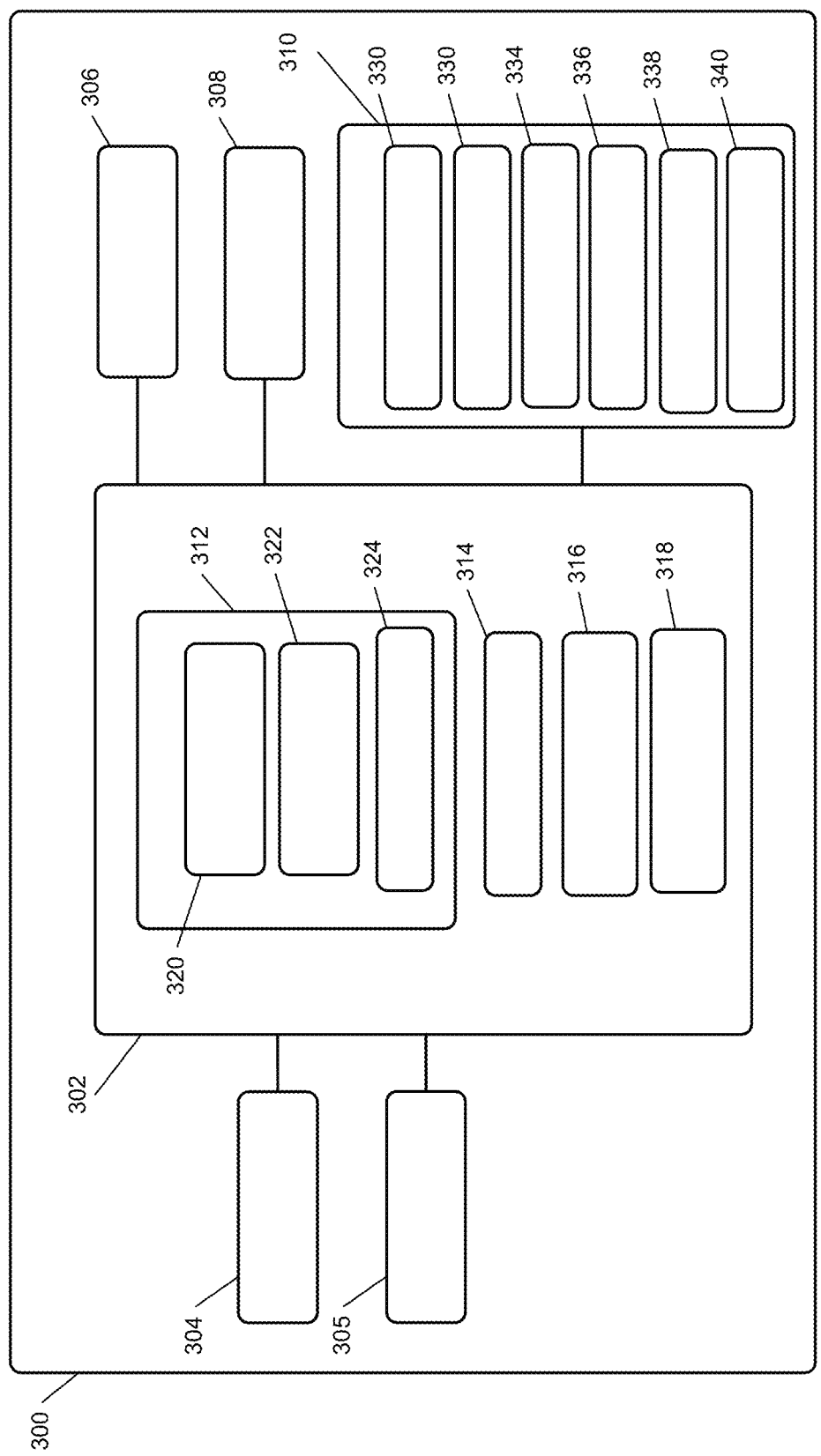
FIG. 3 is a functional block diagram of an example of a portable network device including contamination, cleaning, exposure reporting and risk assessment modules in accordance with the present disclosure.

FIG. 3 shows a portable network device 300 including a control module 302, a transceiver 304, sensors 305, a display 306, an audio system 308, and a memory 310. The portable network device 300 may replace any of the network devices 102 of FIG. 1. The portable network device 300 may be a separate network device, such as a mobile phone, a tablet, a wearable device, or may be integrated and/or embedded in a vehicle and/or other supporting structure. The control module 302 may include a view finder module 312, a cleaning application 314, an exposure reporting application 316, and/or a risk assessment application 318. The applications 314, 316, 318 may be activated via respective icons shown on the display 306.

The view finder module 312 may include a contamination module 320, a sanitization module 322 and/or a localization module 324. The view finder module 312 may determine a location and orientation of the portable network device 300 based on signals from the sensors 305. The sensors 305 may include cameras, global positioning sensors, accelerometers, a gyroscope, etc. Position, location and orientation of the portable network device 300 may be determined by the control module 302 and/or by, for example, one or more of the modules 202, 204, 206 of the supporting structure of FIG. 2 and then shared with the portable network device 300 and/or supporting structure 200. The view finder module, based on the location and orientation, may display contamination and/or sanitization information over a current view seen by one of the cameras. The contamination module 320 may determine the contamination levels of surfaces and/or areas displayed. The sanitization module 322 may determine sanitization levels of surfaces and/or areas displayed. The contamination and sanitization information may be received from a supporting structure and/or a server, such as one of the supporting structures and/or servers of FIGS. 1-2. The localization module 324 may associate the location and the orientation of the portable network device 300 with a surrounding environment and nearby surfaces and/or surfaces in a field of view of the one of the cameras.

The cleaning application 314 may display cleaning information indicating surfaces and/or areas to clean, areas that have been cleaned, when the areas were last cleaned, surfaces that were last cleaned, when the surfaces were last cleaned, probability levels of whether certain surfaces and/or areas have been cleaned, etc. FIG. 5 illustrates an example showing contamination levels. The cleaning application 314 may provide similar overlapping images for levels of cleanliness and/or levels of sanitization.

The exposure reporting application 316 may receive exposure information from one or more servers, such as one of the servers of FIG. 1. For example, the PHAS 106 of FIG. 1 may send exposure information indicating that the portable network device may have been contaminated and/or exposed due to being within close proximity to another network device that was reported as being exposed. This information may be indicated via an alert message on the display 306 and/or via the audio system 308. The audio system 308 may include a speaker, a headset, and/or other audio device.

The control module 302 while executing the risk assessment application 318 may operate similarly as the risk assessment module 228 of FIG. 2 and determine risk levels of exposure to a virus if an individual, for example, enters a vehicle, enters a room, is within a certain location, does a certain activity, contacts a certain surface, etc. This information may be indicated in relationship to where the portable network device 300 is located. For example, if the portable network device is in close proximity to a vehicle and/or is about to enter a vehicle, the risk assessment application 318 may indicate the risk level of contracting a virus if the user of the portable network device 300 enters the vehicle and/or sits in a certain location within the vehicle. Similar indications may be provided when the portable network device is about to enter a particular room, a building, and/or other supporting structure of concern. The risk assessment application 318 may perform these calculations or may receive this information from the risk assessment module 228 of FIG. 2 and/or the risk assessment server 108 of FIG. 1.

Applications similar to the applications 314, 316 and 318 may be implemented by the infotainment module 204 of the supporting structure 200 of FIG. 2. For example, these applications may be implemented by a network device of a vehicle and convey similar information via a display, a projector, and/or an audio system.

The memory 310 may store contamination data 330, sanitization data 332, localization data 334, cleaning data 336, exposure information 338, and/or risk assessment information 340. The stated data may be generated, received, and/or shared by the modules 302, 312, 320, 322.

Figure 4:
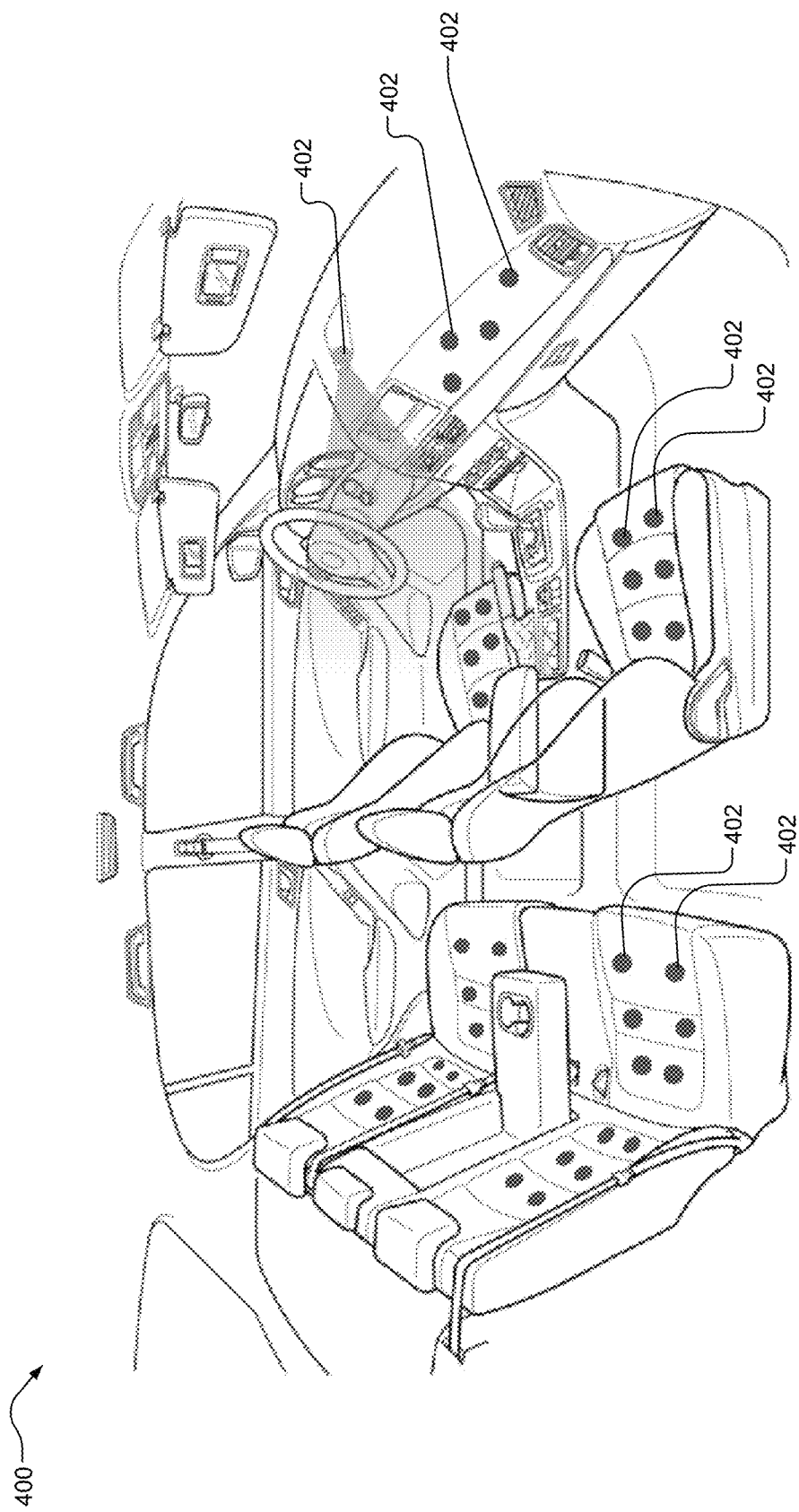
FIG. 4 is a side perspective view of an example of an interior of a vehicle with activity tracking and contact sensors in accordance with the present disclosure.

FIG. 4 shows an interior 400 of a vehicle with activity tracking and contact sensors 402. The activity tracking and contact sensors 402 may include cameras, touch sensors, pressure sensors, etc. The cameras may be located in various locations and track activity. The cameras may include birds-eye cameras, ceiling mounted cameras, cameras mounted on a dashboard and/or a pillar, and/or other cameras. Overhead, front, side, rear and angled camera views may be captured and displayed. The pressure sensors may be located in, for example, seats of the vehicle and detect when an occupant is sitting in a particular seat. The touch sensors may be located in various components, panels, armrests, control actuators (e.g., knobs, buttons, dials, etc.), and/or elsewhere in the vehicle. The touch sensors may detect when an occupant has touched a particular location.

FIG. 5 shows an interior 500 of a vehicle illustrating an augmented reality view via a portable network device 502. The portable network device 502 is held up by a user in front of a vehicle interior to show highlighted touch points. The portable network device 502 may be configured as one of the network devices 102 of FIG. 1 and/or the portable network device 300 of FIG. 3. The portable network device 502 may overlay contamination information on a live view of the interior 500. The user may point the camera of the portable network device 502 in different directions within the interior 500 in order to see the levels of contamination on various interior surfaces.

In the example shown, the contamination information is shown as highlighted areas having different colors and/or shading to indicate different levels of contamination. The types of contacts, the durations of contacts, the number of times contacted, etc. may be translated to different colors and color saturation levels. As a simple example, highly contaminated surfaces may be in red (and have numerical designators 504), intermediately contaminated surfaces may be in yellow (and have numerical designators 506), and surfaces with low or no contamination may be green (and have numerical designators 508). An infinite range of colors and levels of shading may be provided to illustrate the levels of contamination. Similar views may be provided to show levels of sanitization. For example, poorly cleaned areas or areas that have not been cleaned may be in red, moderately cleaned areas may be in yellow, and thoroughly sanitized areas may be in green. Surfaces that are not observed by cameras, sensors and/or feature activation tracking may be encoded with gray coloring in order to denote system uncertainty of the contamination and/or sanitization states of these surfaces. The activity tracking may include cleaning activities including durations surfaces are cleaned and identifying surfaces and/or portions thereof that have been cleaned, partially cleaned and/or not cleaned. A cleaning mode may be activated to allow displayed markings to be removed as surfaces are cleaned.

As an alternative to showing different colors and/or shading, different values and/or percentages may be displayed indicating contamination levels, probability levels of being contaminated, and/or probability levels of contracting a virus if an individual is in contact with and/or in close proximity to the surfaces. This may be based on duration of contact and/or amounts of time being in contact and/or close proximity of the surfaces.

Additional information may also be displayed. This may include additional contextual information, such as a location of the vehicle when contacts have occurred. For example, this information may indicate if the vehicle was in a highly polluted area when the contacts were made indicating that the contamination levels of the contacts may be higher than if the contacts were made in a low pollution area. The information may include cleanliness information and/or antimicrobial and/or antiviral surface material indications and/or decay rates.

The portable network device 502 includes an interior facing camera. The vehicle includes sensors and an internal network for tracking states of components and/or devices to track items touched and/or actuated by an occupant to control and/or change state of a vehicle feature. A vehicle feature may refer to a window, door, mirror, lights, information displayed, infotainment features, stereo selections, navigation selections, etc. The vehicle may report the track contact activity to the and/or the contamination information to the portable network device 502, which may then display images with contaminated areas highlighted, as shown. The portable network device 502 may show, as an example, that stereo controls were touched, steering wheel controls were touched, etc. Feature tracking may be performed by any and/or all of the modules 204, 220, 222, 224 of FIG. 2 to identify controls that have come in physical contact with humans. When a specific feature is engaged, it may be inferred that the control required to activate the feature has been touched, unless voice activated. Tracked features may include infotainment controls and screens, primary controls (e.g., steering, gear shifters) wiper controls, window controls, mirror adjustment controls, interior door handles, etc.). Instances of surface contacts and associated locations are recorded from various sources, centrally aggregated and then shared.

Touch points are recorded and aggregated to create a visual map of likely contamination points, which may be viewed using an in vehicle or mobile application, a virtual reality device (VR), an extended reality (XR) device or a mixed reality (MR) device. The visual map may be viewed using a non-mobile application. The visualization may be a virtual or mixed reality visualization. The mobile application includes various views of the interior and also an AR view in which touched surfaces may be viewed with greater detail through a view-finder of the portable network device 502. This may be done to efficiently identify areas to be avoided by passengers of the vehicle.

Figure 6:
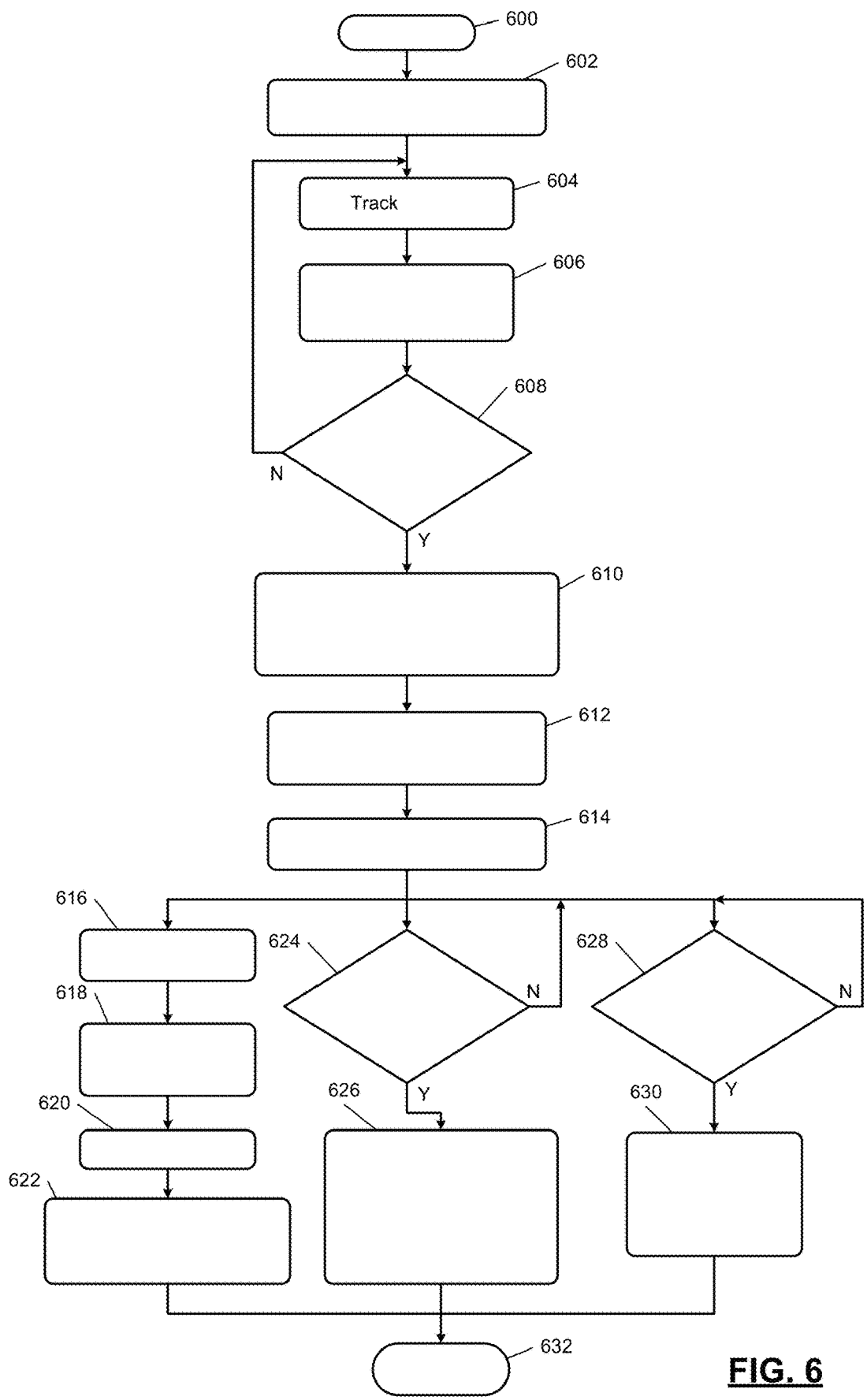
FIG. 6 illustrates a surface contamination indication method in accordance with the present disclosure.

FIG. 6 shows a surface contamination indication method. Although the following operations are primarily described with respect to the implementations of FIGS. 1-3, the operations may be easily modified to apply to other implementations of the present disclosure. The operations may be iteratively performed. The method may begin at 600. At 602, the contamination detection and notification system 201 may be activated and/or initialized. The system 201 may be initialized, for example, when an area being monitored is fully sanitized. All contamination values may be reset to, for example, a null or initial state. As surfaces and/or areas become more and more contaminated, the contamination values may increase.

At 604, the activity tracking module 224 tracks activity based on information received from the sensors 123, 210 and the indicator input devices 125, 208. At 606, the activity tracking module 224 stores the collected activity data and may report the activity data to, for example, the risk assessment server 108 and/or the central monitoring station 110.

At 608, the modules 220, 222 may determine whether requests have been received to show a contamination map and/or a sanitization map of a given area. If yes, operation 610 may be performed. For example, a user may start a contamination and/or sanitization application on a portable network device and/or in the vehicle using a vehicle infotainment system.

At 610, the infotainment module 204 may collect and/or receive localization, contamination, sanitization, cleaning, alert, and/or other information from a remote server, (e.g., the PHAS 106 and the risk assessment server 108). The modules 220, 222 may convert the activity data to contamination and/or sanitization data, which may include visual data, such as surface location and/or identification information and corresponding contamination and sanitization levels. At 614, the infotainment module 204 may store received and/or generated data, which may include received contamination and/or sanitization levels, in memory 212.

At 616, the infotainment module 204 may generate a report and at 618 display the status report. The status report may indicate the contamination levels, sanitization levels, when surfaces were last contacted, when surfaces were last cleaned, estimated indications of how well the surfaces were cleaned, etc.

At 620, the infotainment module 204 may analyze the report 620 to determine: areas and/or surfaces to stay away from until cleaned; areas and/or surfaces that need cleaning; areas and/or surfaces that have low associated risk of someone becoming contaminated and/or contracting a virus; and/or other status information.

At 622, the infotainment module 204 may generate via one or more of the transceivers 235 alert signals indicating areas of high risk and/or that need to be cleaned. This allows for efficiencies in cleaning. Areas that need to be cleaned are identified and cleaned, whereas other areas that do not need to be cleaned are avoided. This decreases amounts of time and/or costs associated with cleaning.

At 624, the infotainment module 204 may determine whether a request has been received to show contamination and/or sanitization results. If yes, operation 626 may be performed. At 626, the modules 220, 222 may display contamination and/or sanitization indications and/or indicators. In addition and/or as an alternative the contamination and/or sanitization information may be transmitted to the portable network device 300. The portable network device 300 may then display this information, as described above.

At 628, the infotainment module 204 may determine if a request has been received to operate in a surface indication mode. If yes, operation 630 may be performed. At 630, the infotainment module 204 may display contamination and/or sanitization indications via smart surfaces, as described above. Subsequent to operations 622, 626, 630, the method may end at 632.

As an example implementation, a rideshare passenger may have interest in taking special care when taking a taxi. The rideshare passenger prior to entering the taxi may start an exposure reporting application (or AR-enabled contact tracking application) such as that described above on a portable network device. The exposure reporting application may be interfaced with a rideshare application, which may also be implemented on the portable network device. The portable network device may contact, for example, a central monitoring station to obtain contamination information associated with the taxi. The passenger may scan via a camera of the portable network device a backseat area of the taxi and see that there has been a high concentration of contact instances of previous passengers around the left-hand side seat and door handle. The passenger may also see that the armrest on that side of the vehicle has not been cleaned for a long time, whereas the right-hand side is shown as having less traffic and contact activity. The passenger may then avoid that area of the back seat and sit on the right-hand side of the backseat. Alternatively, the passenger may clean the armrest and/or other surfaces with, for example, a disinfecting wipe and because of the actions completes the trip with a better piece of mind.

As another implementation example, a retail driver may plan on lending her vehicle to her grandparents while the grandparent's vehicle is being serviced. Due to risks imposed by a pandemic, the retail driver may want to sanitize areas in the vehicle that she or other passengers have previously touched. Before providing the vehicle to her grandparents, she opens the exposure reporting application (or contacting application) included in an infotainment system of the vehicle. The exposure reporting application may be executed by, for example, one of the modules 204, 220, 224 of FIG. 2. The exposure reporting application may then provide contamination and sanitization information via output devices of the vehicle. Based on this information she is able to efficiently locate the contacted surfaces and comprehensively wipe down all of the surfaces and does not have to worry about missing any touched surfaces.

As yet another implementation example, a fleet manager for a company that transports potentially hazardous materials and may institute a new policy that requires drivers to wipe down their vehicles. The fleet manager initiates execution of an exposure tracking application via a central monitoring station control module (e.g., the control module 131 of FIG. 1) in order to help enforce this new policy and track cleanliness of the vehicles. The manager is able to centrally monitor the state of the vehicles and reach out to the drivers to improve the cleanliness level and issue reprimands if requested cleaning tasks are not performed. The manager is able to easily view a dashboard overview of the entire vehicle fleet without having to individually investigate each vehicle. The manager is able to see what areas are commonly missed by the drivers and issue informed advice on improved cleaning practices. The manager may feel more comfortable with this system in place due to less potential liability issues. The drivers are happier about the more efficient cleaning afforded to them due to them not having to clean the entire vehicles, but rather only areas that are contaminated and/or have been contacted and/or exposed.

The systems disclosed herein provide data and insights about vehicle use and occupant interactions that identify health risk exposures during usage of a vehicle as well as prioritizing most significant risk activities and suggesting targeted cleaning maintenance. The disclosed in-vehicle and/or cloud-based systems may risk-prioritize vehicle interactions and based on this information generate sanitization requests. Vehicle decontamination guidance is provided based on understanding vehicle usage activities. Analysis of vehicle sensors, vehicle indicator input devices, vehicle hygiene schedules, positive human health risk exposures and health event notifications are used to determine hygiene countermeasures.

Figure 7:
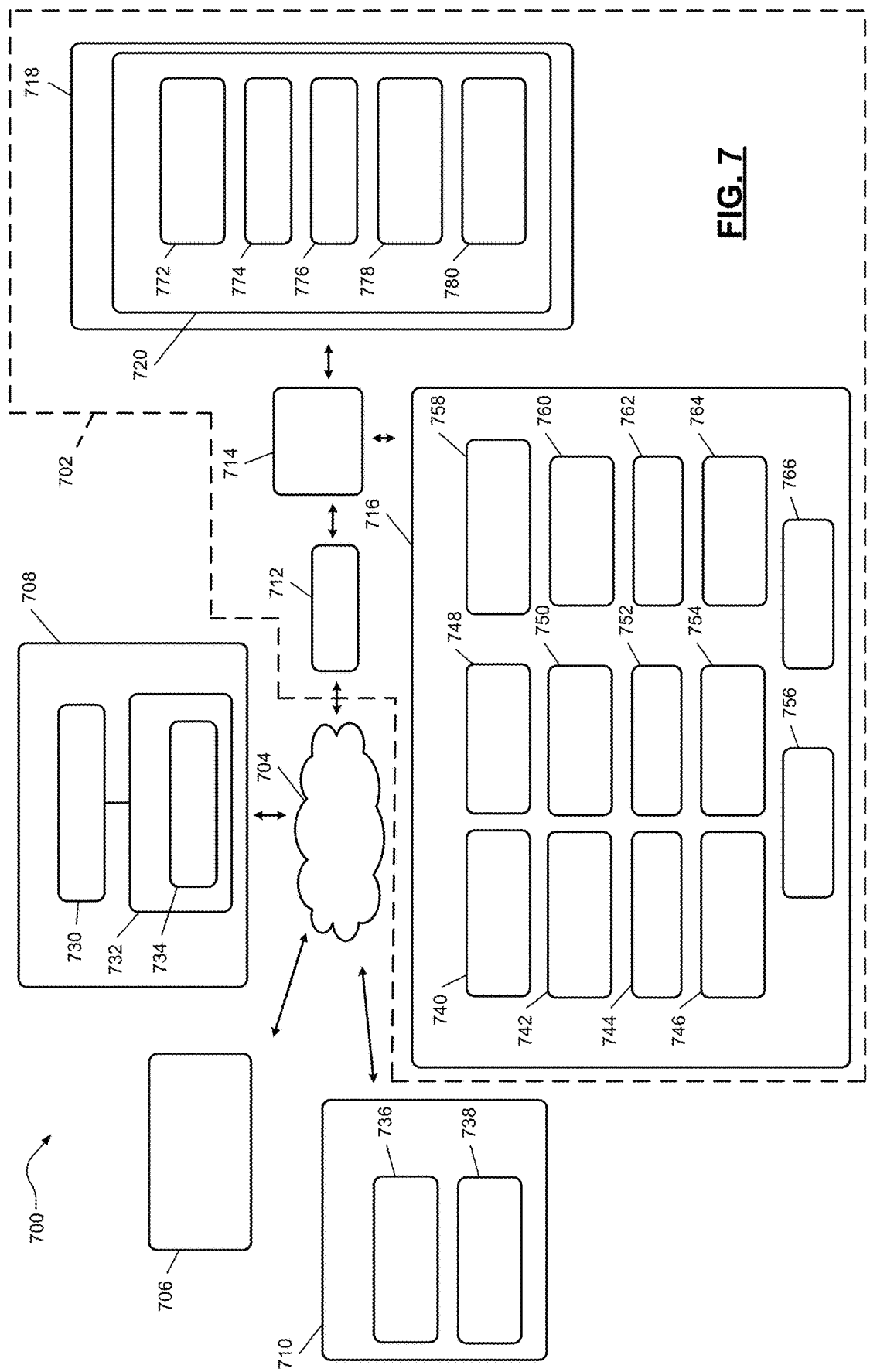
FIG. 7 is a functional block diagram of an example of another risk assessment system in accordance with the present disclosure.

Although the following FIG. 7 is primarily described with respect to a vehicular application, a similar configuration and operations may be performed for other supporting structures. FIG. 7 shows another risk assessment system 700 that may include a vehicle 702, a distributed network 704, a PHAS 706, a risk assessment server 708 and off-board sensors 710. The vehicle 702 may include a transceiver 712, a supporting structure control module 714, on-board sensors 716 and output devices 718 providing notification outputs 720.

The PHAS 706 may operate similarly as the PHAS 106 of FIG. 1. As another example, the PHAS 706 may collect diagnosis keys from users that have been diagnosed as testing positive for a virus (e.g., COVID-19). The PHAS 706 when polled may distribute the diagnosis keys to network devices the users of which have come in close contact with the users that have been diagnosed as having the virus.

The risk assessment server 708 may operate similarly as the risk assessment server 108 of FIG. 1 and may include a control module 730 and a memory 732 that stores an activity history log 734, similar to the activity history log 126 of FIG. 1.

The off-board sensors 710 includes cameras 736 and other infrastructure sensors 738 providing data to the risk assessment server 708 and/or the supporting structure control module 714. The sensors 736, 738 may be located away from the vehicle 702, but in proximity to the vehicle to be able to monitor activity, such as a person accessing the vehicle 702 and/or coming in contact with the vehicle 702. The other infrastructure sensors 738 may include lidar sensors, radar sensors, ultrasonic sensors, infrared sensors, and/or other motion, distance, and/or object detection sensors.

The transceiver 712 may be in communication with the risk assessment server 708 and the PHAS 706 and receive data from the off-board sensors 710. The on-board sensors 716 may include sensors implemented on portable network devices (referred to as portable network device sensors 740), interior motion sensors 742, interior motion sensors 744, microphones 746, object detection sensors 746, cameras 748, brake sensors 750, steering sensor 752, tire pressure sensor 754, vehicle speed sensor 756, vehicle switch monitoring devices 758, human machine interface (HMI) interaction sensors 760, global positioning system (GPS) sensors 762, accelerometers 764, and/or other sensors 766.

The output devices 718 may include any of the output devices referred to above and provide various information, such as the notification outputs 720. The notification outputs 720 may include notification summary reports 772, audio alerts 774, video alerts 776, alternative visual alerts 778 and a state configuration table 780. The notification summary reports 772 may include contamination and/or sanitization information, which may be communicated via emails, alert messages (e.g., text messages), and/or other notifications to users. The audio alerts 774 may include audio sounds played out on speakers and/or other audio devices indicating the stated information. The video alerts 776 may be provided via displays, driver information centers (DICs), embedded information displays, driving displays, head up displays, instrument clusters, and/or navigation screens. The alternative visual alerts 778 may be provided via inside rearview (ISRV) mirrors, outside rearview (OSRV) mirrors, lights, and/or other alternative visual indicators. The state configuration table 780 may indicate cleanliness levels, air quality levels, when last cleaned indications, Boolean values indicating if cleaned in the last predetermined period, etc. The indicated information may be event-based, time-based, and/or location-based.

The supporting structure control module 714 or the control module 730 of the risk assessment server 708 may perform artificial intelligence and deep learning operations in order to determine contamination and sanitization levels of surfaces and air quality levels. This may be based on the activity history log 734, which is continuously and/or periodically updated (or refreshed) for a last set period of time (e.g., 2-3 weeks). The activity history log 734 may be stored at the risk assessment server 708 as shown and/or at the vehicle 702. The distributed network 704 may access and share the activity history log data and/or the contamination and sanitization information with various network devices, such as other vehicles. The stated data and information may also be shared via vehicle-to-vehicle communication and/or infrastructure-to-vehicle communication. The distributed network 704 may be similar to the distributed network 104 of FIG. 1.

The supporting structure control module 714 and/or the control module 730 may, when determining contamination levels, sanitization levels, and risk levels, perform pattern analysis of collected data. The pattern analysis may be time domain based, frequency domain based, spatial (or distance) domain based and/or based on other relationships. Results of the analysis may be shared with the vehicle 702 (or supporting structure), the server 708 and/or other supporting structures, other servers, and/or portable network devices. Driving activity patterns, sensor output patterns, driving patterns, parking patterns, maintenance cleaning patterns, interior activity patterns, exterior activity patterns and non-visible and/or off-board sensor output patterns may be tracked and evaluated. Time usage patterns, communication patterns, signal signature patterns, and other patterns may be monitored. The pattern analysis results may be used to make risk assessment predictions, provide notifications and make assessments and corrections as further described below with respect to FIG. 8.

Figure 8:
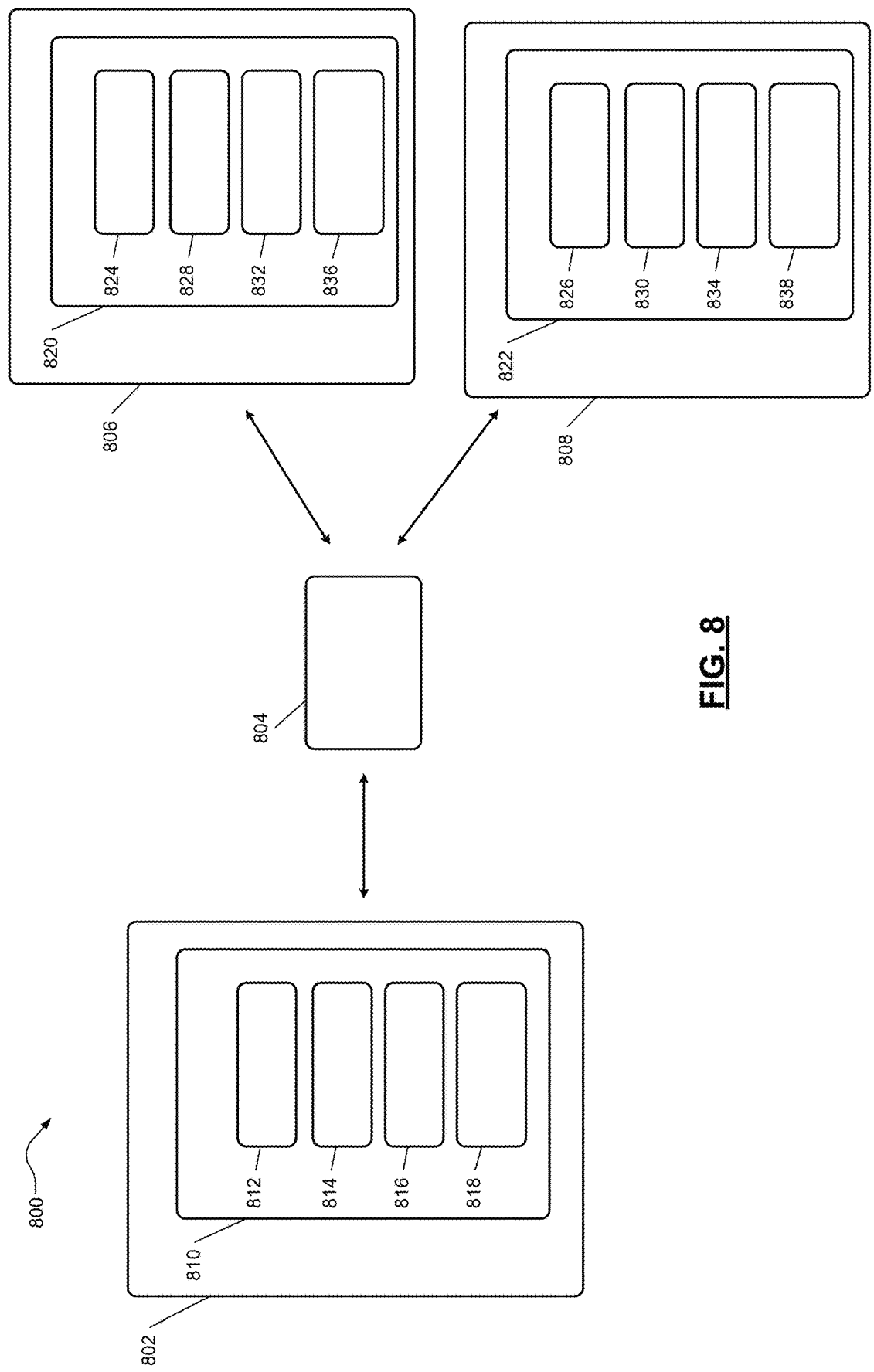
FIG. 8 is a functional block diagram of an example of a vehicular risk assessment system illustrating exposure and risk assessment reporting in accordance with the present disclosure.

FIG. 8 shows a vehicular risk assessment system 800 illustrating exposure and risk assessment reporting. The vehicular risk assessment system 800 may include a vehicle 802, a risk assessment server 804, a first portable network device 806 and a second portable network device 808. The vehicle 802 may include a vehicle control module 810, which may include a monitoring and tracking module 812, a prediction module 814, a notification module 816 and a risk assessment and correction module 818. The modules 812, 814, 816 and 818 may be implemented in a vehicle infotainment module, a body control module, and/or other vehicle control module.

The risk assessment server 804 may be configured and operate similarly as the risk assessment servers 108 and 708 of FIGS. 1 and 7.

The portable network devices 806, 808 may be any type of portable network device stated above and may include respective control modules 820, 822. The control modules 820, 822 may include monitoring and tracking modules 824, 826, prediction modules 828, 830, notification modules 832, 834 and risk assessment and correction modules 836, 838.

The monitoring and tracking modules 812, 824, 826 may track activities and contamination and sanitization levels. The prediction modules 814, 828, 830 may predict (or estimate) exposure risk levels and/or risk levels for contracting a virus. In one embodiment, the prediction modules 814, 828, 830 are implemented as higher order logic applications, which may communicate with one or more of the servers disclosed herein. The one or more servers may be implemented in a cloud-based network. When an event occurs (e.g., a user is reported as testing positive for a virus), other user network devices may be alerted. The prediction modules 814, 828, 830 may analyze activity data to determine whether the other user network devices have been likely exposed. This may be based on locations of the devices, durations of possible exposure, and areas of potential exposure risk intensity levels.

The notification modules 816, 832, 834 may generate messages and/or images to alert a user of risk levels and/or to provide recommended maintenance (or cleaning) recommendations. The notifications may indicate target areas and/or surfaces that should be cleaned. This may be done via a wireless connection (e.g., a Bluetooth® connection, a WLAN connection, and/or a wireless fidelity (WiFi) connection) between the vehicle 802 and the portable network devices 806, 808. As an example, the user of the first network device 806 may send a signal via the first network device 806 to the PHAS 106 or 706 of FIGS. 1 and 7 that the user has a virus (e.g., has tested positive as having a virus) and/or has been exposed to (e.g., has been within a predetermined range of) someone that has a virus. The PHAS 106 or 706 may then signal the vehicle control module 810, the risk assessment server 804 and/or the control module 822 of the second portable network device 808 that the first portable network device 806 has been exposed to a virus.

The vehicle control module 810 and/or the risk assessment server 804 may determine whether the second portable network device 808 has been within a predetermined range of the first portable network device 806. This may be determined based on determined locations of the portable network devices 806, 808 and/or signals transmitted to and from the portable network devices 806, 808. If the second portable network device 808 has been within the predetermined range within a predetermined period of discovering that the first portable network device 806 has been exposed, then an alert signal may be provided at the vehicle 802 and/or at the second portable network device 808 informing the user of the second portable network device 808 of the potential exposure. Similar operations may be performed for other network devices including vehicle network devices that have been potentially exposed to and/or interacted with a portable network device, which has been identified as being exposed.

A manufacturer's vehicles and/or backend servers providing services for the vehicles may be enabled with the above-described systems and modules as part of an ecosystem. This allows quick reporting to users of the network devices that may have been exposed and/or the respective probabilities that they have been exposed.

The risk assessment and correction modules 818, 836, 838 may monitor and track activities in and near the vehicle 802 and activities of the portable network devices 806, 808. This may be based on historical user actions when certain activities are performed. For example, it may be known that an occupant is likely to sit in a certain location for a certain period of time and thus an exposure risk level may be predicted for the associated action. Different risk levels may be provided for different areas of a vehicle. The risk assessment and correction modules 818, 836, 838 may make risk assessment corrections as information updates are received and then report the updates to users of the vehicle and/or network devices 806, 808.

The risk assessment server 804 may perform arbitration operations to determine risk levels. This may include collecting keys of information associated with logging network device and/or vehicle activities in certain geographical locations. The keys may be received from network devices and/or other servers and/or created at the risk assessment server 804. The risk assessment server 804 may then relate the collected information to determine the corresponding exposure risks.

As another example, the network devices 806, 808 may register to a particular network of the vehicle 802. When an exposure event occurs, because these network devices 806, 808 have been paired in time and an identifier of one of the network devices 806, 808 is identified as exposed, then it may be determined based on the signal signature of exposed network device whether the other one of the network devices 806, 808 is nearby the exposed network device. If yes, the other one of the network devices 806, 808 may be alerted that someone positive is near and/or has been near the vehicle 802. The vehicle control module 810 may arbitrarily see if any network devices are paired with and/or are associated in time and space with the exposed network device and provide similar alerts.

The vehicle 802 and the portable network devices 806, 808 are part of a notification network. The vehicle 802 and the portable network devices 806, 808 and/or other network devices in the notification network exchange anonymous identifier keys indicating activity history log information, locations, exposure information, risk assessment information, contamination information, sanitization information and/or other related information disclosed herein. This information may also be shared with any of the servers referred to herein. The sharing may be performed anonymously.

Figure 9:
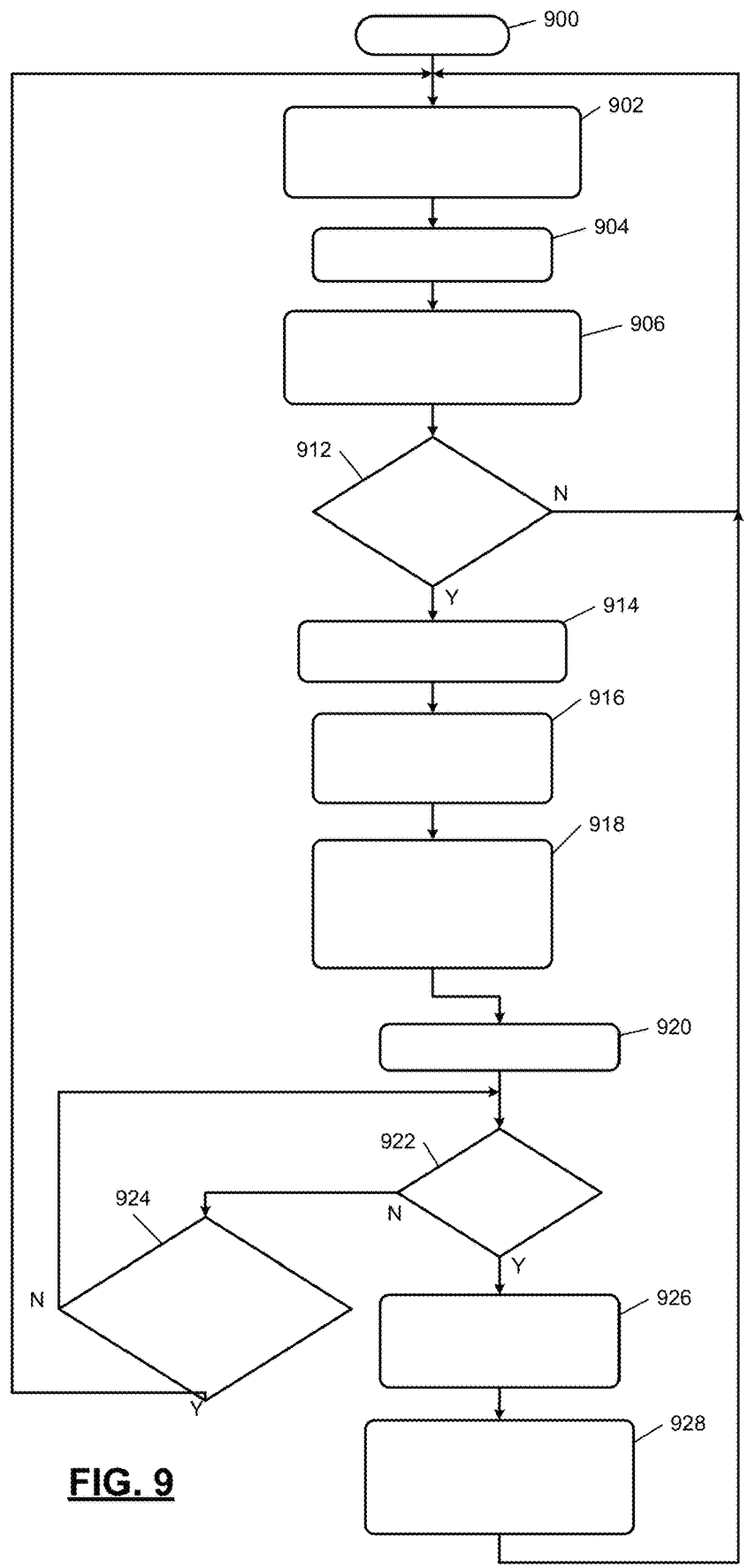
FIG. 9 illustrates a risk assessment method in accordance with the present disclosure.

FIG. 9 shows a risk assessment method, which may be performed to determine exposure risk levels for an individual coming near and/or entering a supporting structure. The method is implemented to alert individuals about potential health risks of potential exposure of a virus based on prior supporting structure activities. The alerts may occur prior to, during and/or subsequent to be exposed to the supporting structure. This method provides health risk awareness to users, occupants, customers, vehicle fleet owners, fleet managers, and/or other individuals. The disclosed systems via, for example, one or more of the modules 202, 204, 302 of FIGS. 2-3 may detect when an individual is approaching and/or is in a supporting structure, determine that the individual may have a potential health risk exposure, and inform the individual via the output devices 211, 260, 306, 208 of the potential health risk exposure. This may be based on sensor data, states of indicator input devices, etc. and provides health risk awareness. The method also includes requesting and tracking decontamination events.

Although the following operations are primarily described with respect to the implementations of FIGS. 1-3, the operations may be easily modified to apply to other implementations of the present disclosure. The operations of this method may be iteratively performed. The method may begin at 900. At 902, the infotainment module 204 may confirm that an embedded exposure notification application and/or the like is being executed by a module of the supporting structure 200. As an example, an embedded exposure notification application may be implemented by any of the modules 204, 214, 220, 222, 224, 226, 228 and perform any of the above described operations associated with the modules 204, 214, 220, 222, 224, 226, 228.

At 904, the activity tracking module 224 logs relevant actions and activities (e.g., vehicle actions and activities) and maintains a rolling log of corresponding data. This may be for a last set period of time (e.g., 2-3 weeks).

An offboard notification process may be performed by network devices and supporting structures and/or servers other than the supporting structure 200. At 906, one or more of the network devices, the supporting structures, the servers and the infotainment module 204 may transmit an anonymous key to one or more of the other ones of the network devices, the supporting structures, the servers and the infotainment module 204. The anonymous key may include activity history logs of the corresponding network device and/or supporting structure and/or the activity history logs of one or more other network devices and/or supporting structures.

At 912, the infotainment module determines if a notification key has been received from a server (e.g., one of the above-described servers). As an example, the notification key may be received from one of the PHASs 106, 706 of FIGS. 1 and 7 and include information indicating that a network device has been exposed (e.g., used by a user tested as being positive for the virus). The notification key may indicate other network devices that may have been exposed due to being in proximity with the exposed network device. If yes, operation 914 is performed, otherwise operation 902 may be performed. The notification key is provided and monitored to allow the system to determine when individuals of network devices may have a potential health risk exposure.

At 914, the infotainment module 204 obtains the activity history log for the supporting structure 200 and may transmit the activity history log to, for example, the risk assessment server 108 of FIG. 1. The activity history log is obtained to be able to better determine a path of the supporting structure 200 and may also be used to determine a possible contamination path if the support structure 200 had been exposed.

At 916, the risk assessment module 228 may determine whether the supporting structure 200 has potentially been exposed and/or what network devices that have been in the supporting structure 200 that have also been potentially exposed. This may also include performing a risk assessment and determining risk levels associated with the supporting structure 200 and the network devices. The risk levels may be determined as described above and be based on: materials of contact surfaces involved; durations of exposure; and decay rates of viruses on the surfaces of concern.

As an example, an algorithm may be implemented via the risk assessment module 228 and/or via one of the control modules 120, 750, 714 of FIGS. 1 and 7 to determine risk levels, which may then be shared with one or more supporting structures, portable network devices and/or servers. The algorithm may determine risk based on decay and disrupted decay. Various functions and equations may be used. For example, an occupant-vehicle-carrier (OHC) risk value $R_{OHC}$ may be determined using equation 1, where: $R_{OHC}$ is the probability that occupant O is contaminated after the occupant has been exposed to a health risk associated with an interior of the vehicle V due to a previous exposure by a carrier C; $E_{exposure}$ is an exposure function describing increase as a function of exposure time to carrier C (or contaminator C); $D_{away}$ is a decay function describing risk decrease as a function of time away from contaminators; and $D_{cleaning\ method}$ is a decay function of risk decrease as a function of time and method being actively cleaned (e.g., ultraviolet C-band (UVC) treatment).

$$R_{OHC}=E_{exposure}(t_0)*D_{away}(t_1)*D_{cleaning\ method}*E_{exposure}(t_2) \quad (1)$$

As an example, where E and D are exponential increase or decrease functions. If a carrier was in a vehicle for 5 minutes and then the vehicle was empty for 6 hours before a new occupant enters and is in the vehicle for 30 minutes, then $R_{OVC}$ may equal $E_{exposure}(5)*D_{away}(6)*E_{exposure}(30)$, which may equal 1.32*0.25*1.9=0.63=63%, depending on the functions used. The associated score is 63%. As a result a probability that the occupant is contaminated is about 60% because the exposure of the vehicle to the contaminant was for only 5 minutes and six hours had passed prior to the occupant entering the vehicle.

As another example, if the carrier was in the vehicle for 30 minutes and the vehicle was empty for 6 hours before an occupant enters and is in the vehicle for 30 minutes, then $R_{OVC}$ may equal $E_{exposure}(30)*D_{away}(6)*E_{exposure}(30)$, which may equal 1.9*0.25*1.9=0.9=90%, depending on the functions used. The increase exposure to the carrier increases the score and the probability that the occupant is contaminated.

As yet another example, if the carrier was in the vehicle for 5 minutes and the vehicle was near perfectly cleaned before the occupant entered the vehicle and is in the vehicle for 30 minutes, then $R_{OVC}$ may equal $E_{exposure}(5)*D_{away}(6)*D_{cleaning\ method}*E_{exposure}(30)$, which may equal 1.32*0.01*1.9=0.02=2%, depending on the functions used. As a result the probability that the occupant is contaminated is drastically reduced.

At 918, the risk assessment module 228 may provide alerts and reports indicating which devices have potentially been exposed and corresponding potential risk levels for each of the devices. This may include indicating whether the supporting structure 200 or any portion thereof has been exposed and the risk levels associated with the supporting structure 200 and/or any network devices of the supporting structure 200. The alerts may be displayed within the supporting structure 200 via one or more of the output devices 211 and/or transmitted to one or more network devices that are currently, for example, in the supporting structure 200, are within a predetermined distance of the supporting structure 200, and/or have been in or within the predetermined distance of the supporting structure 200 sometime over a last predetermined period of time.

At 920, the infotainment module 204 may provide remedies to reduce the risk levels. For example, the infotainment module 204 may indicate one or more remedies via one or more of the output devices 211 including areas and/or surfaces to clean, areas and/or surfaces that likely do not need to be cleaned, and areas and/or surfaces for which the infotainment module 204 does not have sufficient data to indicate whether cleaning is needed.

At 922, the infotainment module 204 may monitor activities to detect when the suggested cleaning has been performed and when the suggested cleaning has been performed (i.e. remediation has been performed), operation 926 is performed, otherwise operation 924 is performed.

At 924, the infotainment module 204 may determine whether a predetermined period has last since a last determination of remedies was made. If yes, operation 902 may be performed, otherwise operation 922 may be performed.

At 926, subsequent to the remediation being performed, the infotainment module 204 may reset alert information and activity history log data for the areas, surfaces and/or devices cleaned. This resets the values indicating that the areas, surfaces and/or devices have been cleaned and risk levels are low or 0.

At 928, the infotainment module 204 may update and provide vehicle activity summary and contamination and/or sanitization state(s) via one or more of the output devices 211 and/or signal the information to other network devices.

The above-described operations of FIGS. 6 and 9 are meant to be illustrative examples. The operations may be performed sequentially, synchronously, simultaneously, continuously, during overlapping time periods or in a different order depending upon the application. Also, any of the operations may not be performed or skipped depending on the implementation and/or sequence of events.

The examples set forth herein include methods for tracking areas and surfaces that have been contaminated in order to improve cleaning capabilities and ultimately reduce virus, bacteria and/or pathogen transmission. Traditional vehicle sanitization methods, such as that performed by fleet drivers and managers are inherently inefficient without any indication of which areas require attention and which areas do not require attention. The examples disclosed herein use various technologies working in tandem in order to track contamination and sanitization states of points throughout a vehicle interior. The technologies include cameras (e.g., interior facing, exterior facing, visible, near IR and far IR) for image and video recording and evaluation, monitoring of other sensors (e.g., pressure, temperature, proximity, IR, light, microphone, etc.), and feature activation, deactivation and control tracking. Motion tracking is utilized to determine when movements cause passengers to come in physical contact with surfaces and where the contact points are located. This also includes fusing information from the various sensors and devices.

Contact time durations are tracked in order to provide information regarding when potential viral, chemical and radioactive contaminates have likely decayed. This information is also based on the types of materials of the contacted surfaces. Contact instances may be visualized via a mobile application and/or interface (e.g., a digital display in a cockpit, digital rendering of the cockpit, and/or use of AR to highlight touches surfaces when viewed through a camera of a portable network device (e.g., smart glasses). Contact instances may also be visualized via smart surface indications and projectors (e.g., a light projector).

The disclosed systems may be utilized by: passengers (e.g., members of a rideshare program) to avoid contaminated areas; fleet owners to sanitize areas in a more efficient manner by allowing the fleet owners to identify areas that do not require much attention. Collection and analysis of vehicle cleaning events, exposure times with and without occupants, and other collected and determined data is performed in order to dynamically recalculate and convey health risk estimation. Countermeasures are performed based on vehicle usage data (e.g., scheduled and performed decontamination and maintenance while providing enhanced alerts based on vehicle functions performed. Data and insights are provided about vehicle use and occupant interactions that identify health risk exposures during usage of a vehicle as well as prioritizing most significant risk activities and suggesting targeted cleaning maintenance. This may be implemented via, the risk assessment module 228 and/or the risk assessment servers 108, 708 of FIGS. 1-2 and 7.

The examples include determining potential health risk exposure and notifying vehicle users and occupants. Data analytics and insights about user interaction are used to determine health risk exposure. Risk analysis may be performed after identifying the presence of an occupant in a vehicle. The occupant may then be informed of a potential health risk using a notification network. Countermeasures may be implemented such as providing exposure alerts, cleaning alerts, and information alerts. The countermeasures may include automatic cleaning and/or disinfecting of areas, such as the injection and/or spraying of disinfectant in the areas. The countermeasures are applied based on vehicle usage data granularity (e.g., schedule, vehicle decontamination or maintenance, enhanced alerts based on vehicle function, etc.).

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A risk assessment system comprising:
   a memory configured to store an activity history log associated with a supporting structure;
   an activity module configured to
      receive a plurality of signals from at least one of sensors or electrical devices of the supporting structure, and
      track activities at least one of in or within a set distance of the supporting structure to generate the activity history log;
   a localization module configured to relate the activities to aspects of the supporting structure and generate corresponding localization data, wherein the aspects include surfaces of the supporting structure;
   a transceiver configured to receive a notification key identifying a network device used by a user exposed to a contaminant;
   a first tracking module configured to, in response to the notification key, track contamination states of the aspects of the supporting structure contacted directly or indirectly by the user including the surfaces contacted directly or indirectly by the user;
   a risk assessment module configured to determine an exposure risk level of an occupant of the supporting structure based on the contamination states of the aspects, the localization data and the activity history log; and
   a portable network device configured to i) indicate the exposure risk level to the occupant, ii) determine a location and orientation of the portable network device relative to the supporting structure, and iii) based on the location and orientation of the portable network device, control a display of the portable network device to provide an augmented reality view of the supporting structure including contamination information overlaid on a live view of the supporting structure captured by the portable network device, the contamination information including the contamination states, wherein the augmented reality view includes contamination information having different contamination states for different portions of the same object.

2. The risk assessment system of claim 1, wherein:
   the activity module is configured to
      track activity of the user in the supporting structure, and
      subsequent to tracking the activity of the user, receive the notification key; and
   the risk assessment module is configured to, subsequent to reception of the notification key, determine the exposure risk level of the occupant.

3. The risk assessment system of claim 1, further comprising second tracking module configured to track events including cleaning at least some of the aspects of the supporting structure,
   wherein the risk assessment module is configured to determine the exposure risk level of the occupant based on information defining aspects of the events including cleaning the aspects of the supporting structure.

4. The risk assessment system of claim 3, wherein:
the second tracking module configured to determine sanitization levels of the at least some of the aspects of the supporting structure based on the tracked events including cleaning; and
the risk assessment module is configured to, based on the sanitization levels, determine the exposure risk level.

5. The risk assessment system of claim 1, wherein the risk assessment module is configured to determine the exposure risk level based on exposure times of the supporting structure to the user, duration of time since the support structure was exposed to the user; and times the occupant was exposed to the supporting structure.

6. The risk assessment system of claim 1, further comprising sensors,
wherein the activity module is configured to identify user interaction with at least some of the aspects based on historical human-vehicle interaction activities, and update the activity history log.

7. The risk assessment system of claim 1, wherein the risk assessment module is configured to:
based on the exposure risk level, convey a message via the portable network device to the occupant to clean at least some of the aspects; and
indicate via the portable network device which of the aspects to dean, which of the aspects that do not need to be cleaned, and which of the aspects for which cleaning indications are not available.

8. The risk assessment system of claim 7, wherein the risk assessment module is configured to, based on the exposure risk level, initiate an automated cleaning process to disinfect one or more of the aspects.

9. The risk assessment system of claim 1, wherein the risk assessment module is configured to risk-prioritize vehicle interactions with the user and determine the exposure risk level based on results of the risk-prioritization of the vehicle interactions with the user.

10. The risk assessment system of claim 1, wherein the risk assessment module is configured to determine the exposure risk level of the occupant based on an exposure function for a carrier, a decay function since last exposure, a decay cleaning function, and an exposure function for the occupant.

11. The risk assessment system of claim 1, wherein the risk assessment module is configured to determine the exposure risk level of the occupant based on at least one of a time domain-based exposure pattern, a frequency domain-based exposure pattern, or a spatial domain-based exposure pattern.

12. The risk assessment system of claim 1, wherein the portable network device is configured to control operation of the display to color different surfaces within the supporting structure, as viewed in the augmented reality view, differently based on the contamination information.

13. A risk assessment server comprising:
a memory configured to store an activity history log of a supporting structure, wherein the supporting structure is a vehicle remotely located away from the risk assessment server;
a transceiver configured to receive the activity history log from the supporting structure and a notification key from an arbitration server, wherein the notification key identifies a first network device of a user exposed to a contaminant; and
a control module configured to
in response to the notification key, track contamination states of aspects of the supporting structure contacted directly or indirectly by the user, wherein the contamination states include contamination levels of interior surfaces of the vehicle, and wherein the aspects include the interior surfaces of the vehicle contacted directly or indirectly by the user,
determine an exposure risk level for an occupant of the supporting structure based on the contamination states of aspects, localization data and the activity history log, and
send an alert message indicating the exposure risk level and the contamination levels of the interior surfaces of the vehicle to a handheld portable network device of the occupant to cause a display of the handheld portable network device to display in an augmented reality view of the supporting structure the exposure risk level and the contamination levels overlaid on a live view of the supporting structure, wherein the augmented reality view provided by the handheld portable network device includes different coloring or shading of the interior surfaces to indicate differences in contamination levels of the interior surfaces.

14. The risk assessment server of claim 13, wherein:
the activity history log includes at least one cleaning event and corresponding characteristics; and
the control module is configured to determine the exposure risk level based on the corresponding characteristics.

15. The risk assessment server of claim 14, wherein the corresponding characteristics identify aspects cleaned, length of time each of the identified aspects were cleaned, and identified aspects not cleaned.

16. The risk assessment server of claim 14, wherein the control module is configured to determine sanitization levels of the aspects based on the corresponding characteristics.

17. The risk assessment server of claim 13, wherein the control module is configured to:
determine the exposure risk level of the occupant based on an exposure function for a carrier, a decay function since last exposure, a decay cleaning function, and an exposure function for the occupant; and
determine the exposure risk level of the occupant based on at least one of a time domain-based exposure pattern, a frequency domain-based exposure pattern, or a spatial domain-based exposure pattern.

18. The risk assessment server of claim 13, wherein the augmented reality view provided by the handheld portable network device includes different portions of an object being colored or shaded differently to indicate differences in contamination levels of surfaces of the object.

19. A risk assessment system comprising:
a memory configured to store an activity history log associated with a supporting structure;
an activity module configured to
receive a plurality of signals from at east one of sensors or first electrical devices of the supporting structure, and
track activities at least one of in or within a set distance of the supporting structure to generate the activity history log;
a localization module configured to relate the activities to aspects of the supporting structure and generate corresponding localization data, wherein the aspects include at least one of surfaces, areas, spaces or volumes of the supporting structure;
a transceiver configured to receive a notification key identifying a network device used by a user exposed to a contaminant;

a first tracking module configured to, in response to the notification key, track contamination states of the aspects of the supporting structure contacted directly or indirectly by the user;

a risk assessment module configured to determine an exposure risk level of an occupant of the supporting structure based on the contamination states of the aspects, the localization data and the activity history log;

an infotainment module configured to generate signals based on the contamination states; and smart surfaces on or within the supporting structure, the smart surfaces of the supporting structure being the first electrical devices or other electrical devices configured to, based on the signals, physically change states to indicate the contamination states, wherein material of the smart surfaces is configured to at least one of change in color and change shading indicating the contamination states.

20. The risk assessment system of claim 19, wherein the smart surfaces are configured to change in at least one of color and shading differently to indicate the contamination states.

* * * * *